(12) United States Patent
Fresco et al.

(10) Patent No.: US 6,426,407 B1
(45) Date of Patent: Jul. 30, 2002

(54) RESIDUES FOR BINDING THIRD STRANDS TO COMPLEMENTARY NUCLEIC ACID DUPLEXES OF ANY BASE PAIR SEQUENCE

(75) Inventors: Jacques R. Fresco, Princeton, NJ (US); Bin Liu, San Francisco, CA (US); Lynn C. Klotz, Somerville, MA (US)

(73) Assignees: Codon Pharm., Gaithersburg, MD (US); Princeton Univ., Princeton, NJ (US)

( * ) Notice: Subject to any disclaimer, the term of this patent is extended or adjusted under 35 U.S.C. 154(b) by 0 days.

(21) Appl. No.: 08/473,888

(22) Filed: Jun. 7, 1995

(51) Int. Cl.[7] .................. C07H 21/02; A61K 48/00; C12Q 1/68
(52) U.S. Cl. ............ 536/22.1; 536/23.1; 536/24.3; 536/24.31; 536/24.33; 514/49; 435/5; 435/6; 435/91.2
(58) Field of Search ............. 435/89, 6, 5, 91.2; 536/22.1, 23.1, 24.3, 24.31, 24.33, 25.5, 25.6, 26.71; 514/44

(56) References Cited

U.S. PATENT DOCUMENTS 5,176,996 A * 1/1993 Hogan et al. ............... 435/6
5,352,580 A * 10/1994 Spears et al. ............... 435/6
5,422,251 A * 6/1995 Fresco ...................... 435/91.1
5,545,521 A * 8/1996 Okamoto et al. ............ 435/5

FOREIGN PATENT DOCUMENTS

WO    WO 92/10590    * 6/1992

OTHER PUBLICATIONS

Xiang et al, "A new pyrimidine nucleoside for the PH independent recognition of G–C base pairs by oligonucleotide directed triplex formation", J. Am. Chem. Soc. 116:11155–11156, Nov. 1994.*
Chollet et al, "DNA containing the base analogue 2–aminoadenine: preparation, use as hybridization probes and cleavage by restriction endonucleases", Nucleic Acids Res. 16(1):305–317, 1988.*
Voss et al, "Use of 2,6 diaminopurine in oligonucleotide gene probes", Biochem. Soc. Trans. 17(5):913, Oct. 1989.*
Cheong et al, "Thermodynamic studies of base pairing involving 2,6–diaminopurine", Nucleic Acids Res. 16(11):5115–5122, 1988.*
Cano et al, "Synthesis of oligodeoxyribonucleotides containing 2,6 diaminopurine", Nucleosides Nucleotides 13(1–3):501–509, 1994.*

* cited by examiner

*Primary Examiner*—Jeffrey Fredman
(74) *Attorney, Agent, or Firm*—Rothwell, Figg, Ernst & Manbeck

(57) ABSTRACT

The invention relates to compositions of matter capable of serving as residues for specific binding of third strands to double-stranded complementary nucleic acids of any base-pair sequence.

14 Claims, 21 Drawing Sheets

PURINE

PYRIMIDINE

10 ANGSTROMS

A:AT

10 ANGSTROMS

TA

CG

|← 10 ANGSTROMS →|

|←——— 10 ANGSTROMS ———→|

F1

F2

F3

F4

10 ANGSTROMS

10 ANGSTROMS

10 ANGSTROMS

D:AT

10 ANGSTROMS

F4:CG

10 ANGSTROMS

RESIDUES FOR BINDING THIRD STRANDS TO COMPLEMENTARY NUCLEIC ACID DUPLEXES OF ANY BASE PAIR SEQUENCE

BACKGROUND OF THE INVENTION

1. Field of the Invention

The invention relates to compositions of matter capable of serving as residues for specific binding of third strands to double-stranded complementary nucleic acids of any base-pair sequence.

2. Description of Related Art

Definitions

Before describing related art, it may be useful to define certain terms to be used throughout the specification in describing the present invention:

Canonical base—any one of the standard nucleic acid bases, adenine-A, guanine-G, cytosine-C, thymine-T, uracil-U.

Canonical base pair—the complementary or Watson-Crick base pairs, AT/U and GC, formed from canonical bases.

Canonical base triplet—a base triplet formed by the interaction of a canonical third strand base and a canonical base pair.

Direct base pair—a target base pair with its purine base located in a homopurine strand of a target duplex sequence, i.e., AT/U, GC.

Inverted base pair—a target base pair with its pyrimidine base located in a purine-rich strand of a target duplex sequence, i.e., U/TA, CG. An inverted base pair therefore interrupts the continuity of a homopurine strand sequence.

Triplex motif—triplex stereochemistry as determined by the predominant bases of the third strand binding to a target Watson-Crick duplex with purine-rich, pyrimidine-rich strands and by the orientation of the third strand relative to that of the purine-rich strand of the target. Note that the mode of third strand base or residue H-bonding to the target base pair is characteristic of each motif.

N-residue—a synthetic third strand residue designed to bind with specificity to a particular direct target base pair or inverted target base pair.

Oligonucleotides (third strands) can bind to double-stranded nucleic acids to form triple-stranded helices (triplexes) in a sequence specific manner (Beal and Dervan, *Science* 251: 1360 (1991); Beal and Dervan, *Nucleic Acids Res.*, 20:2773 (1992); Broitman and Fresco, *Proc. Natl. Acad. Sci. USA*, 84:5120 (1987); Fossella, et al., *Nucleic. Acids Res.* 21:4511 (1993); Letai et al., *Biochemistry* 27:9108 (1988); Sun, et al., *Proc. Natl. Acad. Sci. USA* 86:9198 (1989)).

The third strand binding code (a complementarity principle) dictates the sequence specificity for binding third strands in the major groove of double-stranded nucleic acids to form a triple-stranded helix or triplex. The code provides the specificity of third-strand binding for design of gene-based therapeutics that bind specifically to target nucleic acid sequences with little or no non-specific binding to non-target sequences.

Third-strand binding differs from the familiar Watson-Crick complementarity principle (A:T/U and G:C) for the double-stranded helix in two major respects: (1) the third-strand binding code is degenerate, and (2) third strands bind only to double-strands which contain a sequence of adjacent (or run of) purine bases (A or G) in one of the strands, which here will be called the center or core strand. The third-strand binding code is illustrated in the Table 1 below.

TABLE 1

| Center Strand Purine | Third Strand Base | | | | |
|---|---|---|---|---|---|
| | A | U/T | I | G | C |
| A | + | + | + | − | − |
| G | − | − | + | + | + |

In the center of the table, a "+" means the bases are complementary or correspondent, and a "−" means they are not complementary or not correspondent. The bases are: A=adenine (purine); G=guanine (purine); C=cytosine (pyrimidine); T=thymine (pyrimidine); U=uracil (pyrimidine in RNA); I=inosine (purine nucleoside with the universal third-strand binding base hypoxanthine).

A serious practical limitation for stable third-stand binding dictated by the code in Table 1 is the necessity for runs of purines in the center target strand of typically 10 or more bases interrupted by only one or two pyrimidines (hereafter called "purine-rich" sequences or targets). While runs of sufficient length are present in many of the genes and the non-gene DNA (or RNA) of eukaryotes and prokaryotes and their viruses, they are not frequent enough for widespread diagnostic and therapeutic uses. It is therefore desirable to be able to target a duplex nucleic acid segment with a mixed purine and pyrimidine composition in the center strand.

There are a number of "motifs" which further define third-strand binding to purine-rich targets, still in conformity with the third-strand binding code. The motifs define the base-compositional features of the third strand and whether the third-strand binds parallel or antiparallel to the purine-rich target strand (polarity). Motifs thereby define the hydrogen-bonding (H-bonding) schemes of the third-strand bases to the target base pairs. In consequence, the motifs also determine target specificity and nearest neighbor effects on binding. There are five motifs that describe third-strand binding (Sun and Helene, *Current Opinion in Structural Biology*. 3:345 (1993)). Table 2 summarizes the five motifs, which constitute a subset of constraints to the binding code. Thus, the motifs provide further instructions for defining the sequences of different third-strands that can alternatively bind with specificity to the same target. The Table also gives examples of selected analog bases which may be substituted for the standard or canonical A, G, T/U and C third-strand bases.

TABLE 2

| Third-Strand Bases/Strand Polarity | Binding Code | Some Analog Substitutions |
|---|---|---|
| Pyrimidine/parallel | T:AT | me$^5$C$^+$ for C$^+$ |
| | C$^+$:GC | propyne$^5$C$^+$ for C$^+$ |
| | | propyne$^5$U for T |
| Purine/parallel (A-rich targets) | A:AT | 2,6 DAP for A$^1$ |
| | G:GC | |
| Purine/antiparallel (G-rich targets) | A:AT | 2,6 DAP for A$^1$ |
| | G:GC | |
| T and G/parallel (high nearest neighhor frequencies for AA, GG in center strand) | T:AT | 7-deaza-2'-deoxy-xanthosine for T |
| | G:GC | |
| T and G/antiparallel (high nearest neighhor frequencies for AG, GA in center strand) | T:AT | propyn$^5$U for T |
| | G:GC | |

In the Binding Code column, the colon indicates third-strand binding of the base to the left of the colon, to at least the center purine base on the immediate right of the colon. The + superscript indicates that the base is in the protonated form when it binds (the energy of binding provides the energy for protonation). 2,6 DAP stands for 2,6 diaminopurine. "Parallel" or "antiparallel" refers to the relation of third-strand polarity in the triplex relative to the purine-rich target strand.

In designing third strands, there are other considerations that can affect the stability of the resulting triplex. Third strands composed of A and G bases, for example, have the potential for several kinds of self structure. Very G-rich third strands tend to form either hairpin or linear helices stabilized by G-tetrads (Fresco and Massoulie, *J. Am. Chem. Soc.*, 85:1352 (1963); Zimmerman, et al., *J. Mol. Biol.*, 92:181 (1975); Gern, et al. *Biochemistry*, 34:2042 (1994)). With more equal portions of A and G bases, linear or hairpin duplexes with AG, AA and GG base-pairs form, as well as the tetraplexes, which have melting temperatures ($T_m$) in the same ranges as do dissociations of such third-strands from target duplex. Such third-strand self structures will obviously weaken third-strand binding by altering the equilibrium from triplex toward the duplex plus self-structured third strand. The processes and compositions of this invention can be utilized to devise third strands with reduced tendency for self-structure.

U.S. Pat. Nos. 5,034,506, 5,166,315 and 5,405,938 are directed to various polymers said to be effective to bind to Watson-Crick base pairs. In contrast to the present invention, however, those patents do not precisely model the stereochemistry of the canonical base triplets; nor do they precisely model the stereochemistry of their designed residues. Instead, they are directed to flexible non-native backbones that, upon triplex formation, are possibly capable of assuming locations acceptable for triplex formation. One concern with this approach is that backbones of greater flexibility than native sugar-phosphate backbones may suffer unacceptable negative entropy changes (positive free energy changes) when they are "frozen" into the helical configuration demanded by triplex stereochemistry. This energetically unfavorable change may prevent stable triplex formation. In addition, those patents show residues only for the pyrimidine/parallel motif, not for the other four known triplex motifs.

WO 94/11534 is directed to third-strand residues which have been designed to bind to modified inverted duplex base pairs. The designed residues bind only to the core or center strand duplex base; and to do so, the center strand base must be modified to possess two hydrogen bonding sites. The necessity of duplex base modification to accomplish third-strand binding makes the invention of little use; in particular, it can have no use in therapeutics, since any disease target from a living organism would not possess the required modified bases that are the targets for such triplex formation.

SUMMARY OF THE INVENTION

The present invention relates to rules and guidelines for designing heterocycles and other structures, and to compositions of matter ("residues") designed by those processes that when incorporated into third strands (with natural or synthetic backbones) make those strands capable of specific binding to complementary double-stranded nucleic acids of any base-pair sequence; that is, without the target requiring a purine-rich strand.

Accordingly, a major object of the present invention is to provide synthetic nucleic acid monomers ("residues"), that when incorporated into an oligonucleotide ("third strand"), or analog oligomer, i.e., a third strand with a synthetic backbone, enables the third strand to form a triple-stranded nucleic acid ("triplex") when hybridized to a double-stranded nucleic acid ("duplex"), wherein the "target region" to which the third strand binds is of substantially any base sequence; that is, it need not include a run of a large number of adjacent purines on one strand. In other words, the residues that are provided will be capable of strong and specific binding to inverted base pairs.

In one aspect, the present invention provides a partially synthetic oligonucleotide containing a backbone having a polarity associated therewith, and nucleotide bases and at least one synthetic residue bound to the backbone, the bases and residue(s) of said oligonucleotide being effective to bind in a sequence-specific manner to a target sequence of a duplex polynucleotide, said oligonucleotide capable of binding in a parallel orientation relative to a purine-rich or designated core or center strand of said duplex, said nucleotide bases comprising pyrimidine bases and/or base analogs thereof, and said residue(s) being substantially planar, such that when the oligonucleotide binds to the target sequence, base triplets are formed among each oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide backbone which is linked to the corresponding residue of the oligonucleotide is from about 7.0 Å to about 8.6 Å;

b) the $\Theta$ value, measured from the C1' atom bound to the base in the core or center strand, to the atom of the oligonucleotide backbone which is bound to the residue, is from about 53° to about 82°;

c) the $\zeta$ value indicating the angle between said imaginary circle radius passing through the atom of the residue which is bound to the oligonucleotide backbone, and the bond vector between the residue and the oligonucleotide backbone, is from about −90° to about +90°; and d) the residue forms a total of at least two hydrogen bonds with one or both bases of the corresponding target base pair of the duplex.

In another aspect, the present invention provides a partially synthetic oligonucleotide containing a backbone having a polarity associated therewith, and nucleotide bases and at least one synthetic residue bound to the backbone, the bases and residue(s) of said oligonucleotide being effective to bind in a sequence-specific manner to a target sequence of a duplex polynucleotide, said oligonucleotide capable of binding in a parallel orientation relative to a purine-rich or designated core or center strand of said duplex, said nucleotide bases comprising purine bases and/or base analogs thereof, and said residue(s) being substantially planar, such that when the oligonucleotide binds to the target sequence, base triplets are formed among each oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide backbone which is linked to the corresponding residue of the oligonucleotide is from about 6.7 Å to about 8.6 Å;

b) the $\Theta$ value, measured from the C1' atom bound to the base in the core or center strand, to the atom of the oligonucleotide backbone which is bound to the residue, is from about 81° to about 125°;

c) the ζ value indicating the angle between said imaginary circle radius passing through the atom of the residue which is bound to the oligonucleotide backbone, and the bond vector between the residue and the oligonucleotide backbone, is from about −100° to about +60°; and d) the residue forms a total of at least two hydrogen bonds with one or both bases of the corresponding target base pair of the duplex.

In another aspect, the present invention provides a partially synthetic oligonucleotide containing a backbone having a polarity associated therewith, and nucleotide bases and at least one synthetic residue bound to the backbone, the bases and residue(s) of said oligonucleotide being effective to bind in a sequence-specific manner to a target sequence of a duplex polynucleotide, said oligonucleotide capable of binding in an antiparallel orientation relative to a purine-rich or designated core or center strand of said duplex, said nucleotide bases comprising purine bases and/or base analogs thereof, and said residue(s) being substantially planar, such that when the oligonucleotide binds to the target sequence, base triplets are formed among each oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide backbone which is linked to the corresponding residue of the oligonucleotide is from about 6.5 Å to about 8.6 Å;

b) the e value, measured from the C1' atom bound to the base in the core or center strand, to the atom of the oligonucleotide backbone which is bound to the residue, is from about 86° to about 128°;

c) the ζ value indicating the angle between said imaginary circle radius passing through the atom of the residue which is bound to the oligonucleotide backbone, and the bond vector between the residue and the oligonucleotide backbone, is from about −45° to about +120°; and d) the residue forms a total of at least two hydrogen bonds with one or both bases of the corresponding target base pair of the duplex.

In another aspect, the present invention provides a partially synthetic oligonucleotide containing a backbone having a polarity associated therewith, and nucleotide bases and at least one synthetic residue bound to the backbone, the bases and residue(s) of said oligonucleotide being effective to bind in a sequence-specific manner to a target sequence of a duplex polynucleotide, said oligonucleotide capable of binding in a parallel orientation relative to a purine-rich or designated core or center strand of said duplex, said nucleotide bases comprising guanine to bind to GC base pairs, and thymine or uracil and/or base analogs thereof, or 2,6-diaminopurine to bind to AT/U base pairs, and said residue(s) being substantially planar, such that when the oligonucleotide binds to the target sequence, base triplets are formed among each oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide backbone which is linked to the corresponding residue of the oligonucleotide is from about 7.0 Å to about 8.6 Å;

b) the ζ value, measured from the C1' atom bound to the base in the core or center strand, to the atom of the oligonucleotide backbone which is bound to the residue, is from about 62° to about 107°;

c) the ζ value indicating the angle between said imaginary circle radius passing through the atom of the residue which is bound to the oligonucleotide backbone, and the bond vector between the residue and the oligonucleotide backbone, is from about −90° to about +90°; and d) the residue forms a total of at least two hydrogen bonds with one or both bases of the corresponding target base pair of the duplex.

In another aspect, the present invention provides a partially synthetic oligonucleotide containing a backbone having a polarity associated therewith, and nucleotide bases and at least one synthetic residue bound to the backbone, the bases and residue(s) of said oligonucleotide being effective to bind in a sequence-specific manner to a target sequence of a duplex polynucleotide, said oligonucleotide capable of binding in an antiparallel orientation relative to a purine-rich or designated core or center strand of said duplex, said nucleotide bases comprising guanine to bind to GC base pairs, and thymine or uracil and/or base analogs thereof or 2,6-diaminopurine to bind to AT/U base pairs, and said residue(s) being substantially planar, such that when the oligonucleotide binds to the target sequence, base triplets are formed among each oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide backbone which is linked to the corresponding residue of the oligonucleotide is from about 5.9 Å to about 8.2 Å;

b) the Θ value, measured from the C1' atom bound to the base in the core or center strand, to the atom of the oligonucleotide backbone which is bound to the residue, is from about 90° to about 110°;

c) the ζ value indicating the angle between said imaginary circle radius passing through the atom of the residue which is bound to the oligonucleotide backbone, and the bond vector between the residue and the oligonucleotide backbone, is from about −30° to about +120°; and d) the residue forms a total of at least two hydrogen bonds with one or both bases of the corresponding target base pair of the duplex.

In another aspect, the present invention provides a substantially synthetic oligonucleotide analog containing a backbone having no polarity associated therewith, and nucleotide bases and at least one synthetic residue bound to the backbone, the bases and residue(s) of said oligonucleotide analog being effective to bind in a sequence-specific manner to a target sequence of a duplex polynucleotide, said oligonucleotide analog capable of binding to a purine-rich or designated core or center strand of said duplex, said nucleotide bases comprising pyrimidine bases and/or base analogs thereof, and said residue(s) being substantially planar, such that when the oligonucleotide analog binds to the target sequence, base triplets are formed among each analog oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide analog backbone which is linked to the corresponding residue of the oligonucleotide analog is from about 7.0 Å to about 8.6 Å;

b) the Θ value, measured from the C1' atom bound to the base in the core or center strand, to the atom of the oligonucleotide analog backbone which is bound to the residue, is from about 53° to about 82°;

c) the ζ value indicating the angle between said imaginary circle radius passing through the atom of the residue which is bound to the oligonucleotide analog backbone, and the bond vector between the residue and the oligonucleotide analog backbone, is from about −90° to about +90°; and d) the residue forms a total of at least two hydrogen bonds with one or both bases of the corresponding target base pair of the duplex.

In another aspect, the present invention provides a substantially synthetic oligonucleotide analog containing a backbone having no polarity associated therewith, and nucleotide bases and at least one synthetic residue bound to the backbone, the bases and residue(s) of said oligonucleotide analog being effective to bind in a sequence-specific manner to a target sequence of a duplex polynucleotide, said oligonucleotide analog capable of binding to a purine-rich or designated core or center strand of said duplex, said nucleotide bases comprising purine bases and/or base analogs thereof, and said residue(s) being substantially planar, such that when the oligonucleotide analog binds to the target sequence, base triplets are formed among each analog oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide analog backbone which is linked to the corresponding residue of the oligonucleotide analog is from about 6.7 Å to about 8.6 Å;

b) the Θ value, measured from the C1' atom bound to the base in the core or center strand, to the atom of the oligonucleotide analog backbone which is bound to the residue, is from about 81° to about 125°;

c) the ζ value indicating the angle between said imaginary circle radius passing through the atom of the residue which is bound to the oligonucleotide analog backbone, and the bond vector between the residue and the oligonucleotide analog backbone, is from about −100° to about +60°; and d) the residue forms a total of at least two hydrogen bonds with one or both bases of the corresponding target base pair of the duplex.

In another aspect, the present invention provides a substantially synthetic oligonucleotide analog containing a backbone having no polarity associated therewith, and nucleotide bases and at least one synthetic residue bound to the backbone, the bases and residue(s) of said oligonucleotide analog being effective to bind in a sequence-specific manner to a target sequence of a duplex polynucleotide, said oligonucleotide analog capable of binding to a purine-rich or designated core or center strand of said duplex, said nucleotide bases comprising purine bases and/or base analogs thereof, and said residue(s) being substantially planar, such that when the oligonucleotide analog binds to the target sequence, base triplets are formed among each analog oligonucleotide base or residue and the corresponding bases of the target base pair of the duplex, and each residue conforms to the following parameters:

a) the radius of the imaginary circle connecting the C1' ends of the two glycosyl bonds of the target base pair of the duplex polynucleotide and the atom of the oligonucleotide analog backbone which is linked to the corresponding residue of the oligonucleotide analog is from about 6.5 Å to about 8.6 Å;

b) the Θ value, measured from the C1' atom bound to the base in the core or center strand, to the atom of the oligonucleotide analog backbone which is bound to the residue, is from about 86° to about 128°;

c) the ζ value indicating the angle between said imaginary circle radius passing through the atom of the residue which is bound to the oligonucleotide analog backbone, and the bond vector between the residue and the oligonucleotide analog backbone, is from about −45° to about +120°; and d) the residue forms a total of at least two hydrogen bonds with one or both bases of the corresponding target base pair of the duplex.

In another aspect, the present invention provides a substantially synthetic oligonucleotide analog containing a backbone having no polarity associated therewith, and nucleotide bases and at least one synthetic residue bound to the backbone, the bases and residue(s) of said oligonucleotide analog being effective to bind in a sequence-specific manner to a target sequence of a duplex polynucleotide, said oligonucleotide analog capable of binding to a purine-rich or designated core or center strand of said duplex, said nucleotide bases comprising guanine to bind to GC base pairs, and thymine or uracil or base analogs thereof or 2,6-diaminopurine to bind to AT/U base pairs, and said residue (s) being substantially planar, such that when the oligonucleotide analog binds to the target sequence, base triplets are formed among each analog oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide analog backbone which is linked to the corresponding residue of the oligonucleotide analog is from about 7.0 Å to about 8.6 Å;

b) the Θ value, measured from the C1' atom bound to the base in the core or center strand, to the atom of the oligonucleotide analog backbone which is bound to the residue, is from about 62° to about 107°;

c) the ζ value indicating the angle between said imaginary circle radius passing through the atom of the residue which is bound to the oligonucleotide analog backbone, and the bond vector between the residue and the oligonucleotide analog backbone, is from about −90° to about +90°; and d) the residue forms a total of at least two hydrogen bonds with one or both bases of the corresponding target base pair of the duplex.

In another aspect, the present invention provides a substantially synthetic oligonucleotide analog containing a backbone having no polarity associated therewith, and nucleotide bases and at least one synthetic residue bound to the backbone, the bases and residue(s) of said oligonucleotide analog being effective to bind in a sequence-specific manner to a target sequence of a duplex polynucleotide, said oligonucleotide analog capable of binding to a purine-rich or designated core or center strand of said duplex, said nucleotide bases comprising guanine to bind to GC base pairs, and thymine or uracil and/or base analogs thereof or 2,6-diaminopurine to bind to AT/U base pairs, and said residue (s) being substantially planar, such that when the oligonucleotide analog binds to the target sequence, base triplets are formed among each analog oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide analog backbone which is linked to the corresponding residue of the oligonucleotide analog is from about 5.9 Å to about 8.2 Å;

b) the Θ value, measured from the C1' atom bound to the base in the core or center strand, to the atom of the oligonucleotide analog backbone which is bound to the residue, is from about 90° to about 110°;

c) the ζ value indicating the angle between said imaginary circle radius passing through the atom of the residue which is bound to the oligonucleotide analog backbone, and the bond vector between the residue and the oligonucleotide analog backbone, is from about −30° to about +120°; and d) the residue forms a total of at least two hydrogen bonds with one or both bases of the corresponding target base pair of the duplex.

In another aspect, the present invention provides a method of forming a triple-stranded nucleic acid comprising the steps of:

a) providing a nucleic acid core or center strand which has a target sequence with 50% or more of purine bases;

b) providing a complementary nucleic acid strand which is hydrogen bonded in a Watson-Crick manner to said target sequence on the core or center strand;

c) providing a third nucleic acid oligonucleotide or backbone analog strand comprising a natural or synthetic backbone, in the latter case that is directional or nondirectional, containing nucleotide bases and at least one synthetic residue bound to the backbone, the bases and residue(s) of said third strand being effective to bind in a sequence-specific manner to the target sequence, said nucleotide bases comprising pyrimidine bases and/or base analogs thereof, and said residue(s) being substantially planar; and d) contacting duplex formed from said core or center and complementary strands with said third strand, so as to allow formation of hydrogen bonds between the bases and residue(s) of the third strand and the target sequence of the core or center strand alone or together with the complementary strand, so as to form the triple-stranded nucleic acid, and each residue conforms to the following parameters:

i) the radius of the imaginary circle connecting the C1' ends of the two glycosyl bonds of the target base pair of the duplex polynucleotide and the atom of the oligonucleotide backbone or backbone analog which is linked to the corresponding residue of the oligonucleotide or backbone analog is from about 7.0 Å to about 8.6 Å;

ii) the Θ value, measured from the C1' atom bound to the base in the core or center strand, to the atom of the oligonucleotide backbone or backbone analog which is bound to the residue, is from about 53° to about 82°;

iii) the ζ value indicating the angle between said imaginary circle radius passing through the atom of the residue which is bound to the oligonucleotide backbone or backbone analog, and the bond vector between the residue and the oligonucleotide backbone or backbone analog, is from about −90° to about +90°; and iv) the residue forms a total of at least two hydrogen bonds with one or both bases of the corresponding target base pair of the duplex.

In another aspect, the present invention provides a method of forming a triple-stranded nucleic acid comprising the steps of:

a) providing a nucleic acid core or center strand which has a target sequence with 50% or more of purine bases;

b) providing a complementary nucleic acid strand which is hydrogen bonded in a Watson-Crick manner to said target sequence on the core or center strand;

c) providing a third nucleic acid oligonucleotide or backbone analog strand comprising a natural or synthetic backbone, in the latter case that is directional or nondirectional, containing nucleotide bases and at least one synthetic residue bound to the backbone, the bases and residue(s) of said third strand being effective to bind in a sequence-specific manner to the target sequence, said nucleotide bases comprising purine bases and/or base analogs thereof, and said residue(s) being substantially planar; and d) contacting duplex formed from said core or center and complementary strands with said third strand, so as to allow formation of hydrogen bonds between the bases and residue(s) of the third strand and the target sequence of the core or center strand alone or together with the complementary strand, so as to form the triple-stranded nucleic acid, and each residue conforms to the following parameters:

i) the radius of the imaginary circle connecting the C1' ends of the two glycosyl bonds of the target base pair of the duplex polynucleotide and the atom of the oligonucleotide backbone or backbone analog which is linked to the corresponding residue of the oligonucleotide or backbone analog is from about 6.7 Å to about 8.6 Å;

ii) the Θ value, measured from the C1' atom bound to the base in the core or center strand, to the atom of the oligonucleotide backbone or backbone analog which is bound to the residue, is from about 81° to about 125°;

iii) the ζ value indicating the angle between said imaginary circle radius passing through the atom of the residue which is bound to the oligonucleotide backbone or backbone analog, and the bond vector between the residue and the oligonucleotide backbone or backbone analog, is from about −100° to about +60°; and iv) the residue forms a total of at least two hydrogen bonds with one or both bases of the corresponding target base pair of the duplex.

In another aspect, the present invention provides a method of forming a triple-stranded nucleic acid comprising the steps of:

a) providing a nucleic acid core or center strand which has a target sequence with 50% or more of purine bases;

b) providing a complementary nucleic acid strand which is hydrogen bonded in a Watson-Crick manner to said target sequence on the core or center strand;

c) providing a third nucleic acid oligonucleotide or oligonucleotide analog strand comprising a natural or synthetic backbone, in the latter case that is directional or nondirectional, containing nucleotide bases and at least one synthetic residue bound to the backbone, the bases and residue(s) of said third strand being effective to bind in a sequence-specific manner to the target sequence, said nucleotide bases comprising purine bases and/or base analogs thereof, and said residue(s) being substantially planar; and d) contacting duplex formed from said core or center and complementary strands with said third strand, so as to allow formation of hydrogen bonds between the bases and residue(s) of the third strand and the target sequence of the core or center strand alone or together with the complementary strand, so as to form the triple-stranded nucleic acid, and each residue conforms to the following parameters:
  i) the radius of the imaginary circle connecting the C1' ends of the two glycosyl bonds of the target base pair of the duplex polynucleotide and the atom of the oligonucleotide backbone or backbone analog which is linked to the corresponding residue of the oligonucleotide or backbone analog is from about 6.5 Å to about 8.6 Å;
  ii) the Θ value, measured from the C1' atom bound to the base in the core or center strand, to the atom of the oligonucleotide backbone or backbone analog which is bound to the residue, is from about 86° to about 128°;
  iii) the ζ value indicating the angle between said imaginary circle radius passing through the atom of the residue which is bound to the oligonucleotide backbone or backbone analog, and the bond vector between the residue and the oligonucleotide backbone or backbone analog, is from about −45° to about +120°; and
  iv) the residue forms a total of at least two hydrogen bonds with one or both bases of the corresponding target base pair of the duplex.

In another aspect, the present invention provides a method of forming a triple-stranded nucleic acid comprising the steps of:
a) providing a nucleic acid core or center strand which has a target sequence with 50% or more of purine bases;
b) providing a complementary nucleic acid strand which is hydrogen bonded in a Watson-Crick manner to said target sequence on the core or center strand;
c) providing a third nucleic acid oligonucleotide or oligonucleotide analog strand comprising a natural or synthetic backbone, in the latter case that is directional or nondirectional, containing nucleotide bases and at least one synthetic residue bound to the backbone, the bases and residue(s) of said third strand being effective to bind in a sequence-specific manner to the target sequence, said nucleotide bases comprising guanine to bind to GC base pairs, and thymine or uracil and/or base analogs thereof, or 2,6-diaminopurine to bind to AT/U base pairs, and said residue(s) being substantially planar; and
d) contacting duplex formed from said core or center and complementary strands with said third strand, so as to allow formation of hydrogen bonds between the bases and residue(s) of the third strand and the target sequence of the core or center strand alone or together with the complementary strand, so as to form the triple-stranded nucleic acid, and each residue conforms to the following parameters:
  i) the radius of the imaginary circle connecting the C1' ends of the two glycosyl bonds of the target base pair of the duplex polynucleotide and the atom of the oligonucleotide backbone or backbone analog which is linked to the corresponding residue of the oligonucleotide or backbone analog is from about 7.0 Å to about 8.6 Å;
  ii) the Θ value, measured from the C1' atom bound to the base in the core or center strand, to the atom of the oligonucleotide backbone or backbone analog which is bound to the residue, is from about 62° to about 107°;
  iii) the ζ value indicating the angle between said imaginary circle radius passing through the atom of the residue which is bound to the oligonucleotide backbone or backbone analog, and the bond vector between the residue and the oligonucleotide backbone or backbone analog, is from about −90° to about +90°; and
  iv) the residue forms a total of at least two hydrogen bonds with one or both bases of the corresponding target base pair of the duplex.

In another aspect, the present invention provides a method of forming a triple-stranded nucleic acid comprising the steps of:
a) providing a nucleic acid core or center strand which has a target sequence with 50% or more of purine bases;
b) providing a complementary nucleic acid strand which is hydrogen bonded in a Watson-Crick manner to said target sequence on the core or center strand;
c) providing a third nucleic acid oligonucleotide or oligonucleotide analog strand comprising a natural or synthetic backbone, in the latter case that is directional or nondirectional, containing nucleotide bases and at least one synthetic residue bound to the backbone, the bases and residue(s) of said third strand being effective to bind in a sequence-specific manner to the target sequence, said nucleotide bases comprising guanine to bind to GC base pairs, and thymine or uracil and/or base analogs thereof or 2,6-diaminopurine to bind to AT/U base pairs, and said residue being substantially planar; and
d) contacting duplex formed from said core or center and complementary strands with said third strand, so as to allow formation of hydrogen bonds between the bases and residue of the third strand and the target sequence of the core or center strand alone or together with the complementary strand, so as to form the triple-stranded nucleic acid, and each residue conforms to the following parameters:
  i) the radius of the imaginary circle connecting the C1' ends of the two glycosyl bonds of the target base pair of the duplex polynucleotide and the atom of the oligonucleotide backbone or backbone analog, which is linked to the corresponding residue of the oligonucleotide or backbone analog is from about 5.9 Å to about 8.2 Å;
  ii) the Θ value, measured from the C1' atom bound to the base in the core or center strand, to the atom of the oligonucleotide or backbone analog which is bound to the residue, is from about 90° to about 110°;
  iii) the ζ value indicating the angle between said imaginary circle radius passing through the atom of the residue which is bound to the oligonucleotide or backbone analog, and the bond vector between the residue and the oligonucleotide or backbone analog, is from about −30° to about +120°; and
  iv) the residue forms a total of at least two hydrogen bonds with one or both bases of the corresponding target base pair of the duplex.

BRIEF DESCRIPTION OF THE DRAWINGS

FIG. 7 is an illustration, drawn to scale, of the definitions of D-circle radius, glycosyl-bond position angle, $\Theta$, and glycosyl-bond orientation angle, $\zeta$. For purposes of illustration, the purine/parallel motif is chosen. The obvious, analogous definitions hold for the other motifs. The D-circle radius, denoted by $r_D$, is that of the unique circle which can be drawn through three points, which in the invention are the three $C_1'$ deoxyribose atoms of the three glycosyl bonds. The center of the circle is located at the intersection of the perpendicular bisectors of any two of the three lines connecting two of the three points. The radius is then the distance from the center to any of the three points. The $\Theta$ value represents the angular displacement of the $C_1'$ atom of the third-strand base from the center or core third-strand residue on the D-circle. Thus, for Z:RY, $\Theta$ is measured clockwise from the $C_1'$ atom of the purine R to the $C_1'$ atom of the third-strand Z base. The $\zeta$ values represent the direction of the glycosyl bond of each triplet base Z. $\zeta$ is measured clockwise as the angle between the D-circle radius and the glycosyl bond origin at the $N_9$ or $N_1$ atoms of the purine or pyrimidine bases, respectively, or in the case of N residues (i.e., the synthetic residues in accordance with the present invention), of whatever atom of the heterocycle the sugar is linked to.

DETAILED DESCRIPTION OF THE INVENTION

Object of the Invention

A major object of the present invention is to circumvent the purine-rich target restriction, thus enabling third strands to bind to duplexes with core or center strands comprising mixed purine/pyrimidine sequences, with the consequence that either strand of the duplex could serve as the center strand and so define the target sequence. In the present invention, the center or core strand is taken to be the duplex strand which is purine rich in the target sequence, i.e., has greater than 50% purines in the target sequence. If both duplex strands contain exactly 50% purines in the target sequence, then either strand may be designated the center or core strand.

The invention particularly provides processes for designing residues that when incorporated into third-strand oligonucleotides or their backbone analogs will bind specifically to "inverted" base pairs; i.e., base pairs with pyrimidines in the designated center strand (which is not allowed under the binding code governing standard bases and inosine, Table 1). Inverted base pairs, therefore, are those that interrupt the runs of purine residues in the center target strand. Another object of the invention is to design novel residues that bind more stably to "direct" base pairs (i.e., base pairs to which the standard bases and inosine bind as allowed by the binding code in Table 1). It is emphasized that the designed residues sometimes bind to both bases in the duplex, not just the base in the center strand. Indeed, according to the present invention, residues designed to bind to inverted base pairs must bind to both bases of the target base pairs.

Formal Definition of an Inverted Base Pair

A useful notation to describe third strands and direct and inverted base pairs is to let Z signify a standard or canonical third-strand base; R the standard or canonical purine bases A and G, and Y the standard or canonical pyrimidine bases T and C in the base pairs of a target duplex. Then, Z:RY denotes a base triplet with base Z bound to a "direct" base pair, that is, a base pair with a purine in the designated center strand. Furthermore, letting N signify a residue designed in accordance with the present invention, then N:YR denotes the base triplet with residue N bound to an "inverted" base pair, and N:RY denotes the base triplet with residue N bound to a "direct" base pair. Since the standard nucleic acid bases and inosine do not bind strongly to inverted base pairs, Z:YR denote "mismatches".

Figure 8:
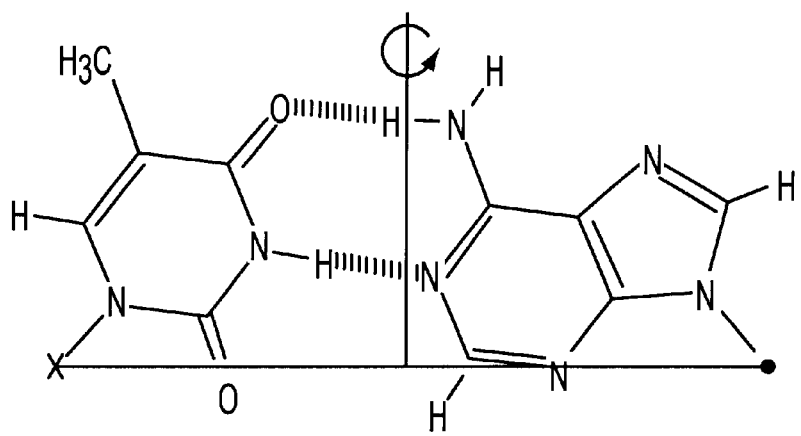
FIG. 8 is an illustration, drawn to scale, of the inverted TA and CG base pairs. Contrast with the direct AT and GC base pairs in FIG. 2.
Figure 8:
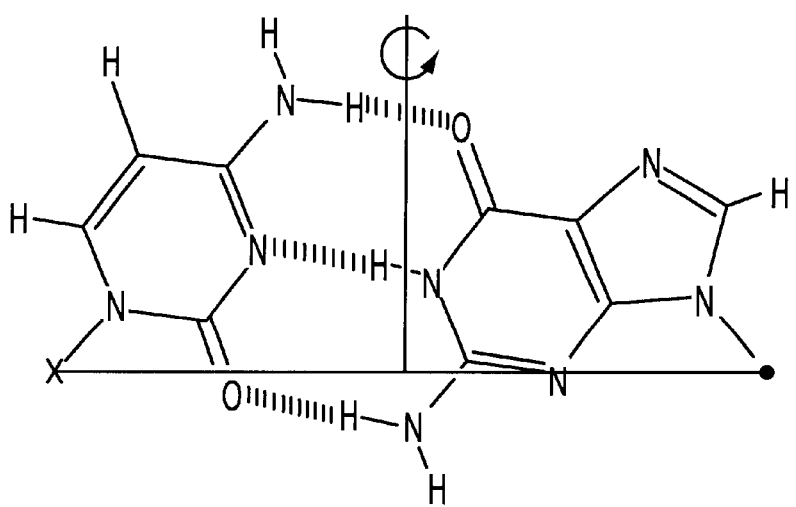
Figure 9:
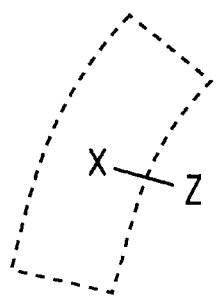
FIG. 9 is a schematic illustration, drawn to scale, summarizing the acceptable range for D-circle radius, $\Theta$ and $\zeta$ for the pyrimidine/parallel motif for designed residues N. The only molecular details shown are the glycosyl bonds, which are drawn with correct length and orientations. The positions of the glycosyl bonds for the canonical base-pairs RY, are denoted by "x" and "o" as in previous figures. The positions of the glycosyl bonds for both canonical third-strand bases T and $C^+$ are denoted by the single letter Z, since in this motif both bonds lie substantially in the same position on the same D-circle. The area surrounded by dots substantially encompasses the acceptable area in which the C1' end of the glycosyl bond of designed W residues can reside, derived from the acceptable ranges in Tables 4, 5 and 6.
Figure 9:
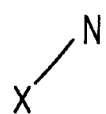
Figure 9:
Figure 9:
Figure 10:
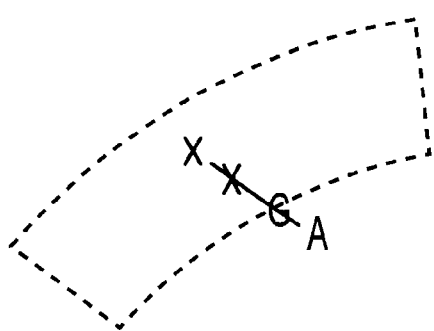
FIG. 10 is a schematic illustration, drawn to scale, summarizing the acceptable range for D-circle radius, $\Theta$ and $\zeta$ for the purine/parallel motif for designed residues N. The only molecular details shown are the glycosyl bonds, which are drawn with correct length and orientations. The positions of the glycosyl bonds for the canonical base-pairs RY, are denoted by "x" and "o" as in previous figures. The positions of the glycosyl bonds for the canonical third-strand bases A and G are denoted by those base letters. Note that the A and G third-strand base glycosyl bonds lie very close to each other and have very similar orientations in this motif. The area surrounded by dots substantially encompasses the acceptable area in which the C1' end of the glycosyl bond of designed N residues can reside, derived from the acceptable ranges in Tables 4, 5 and 6.
Figure 10:
Figure 11:
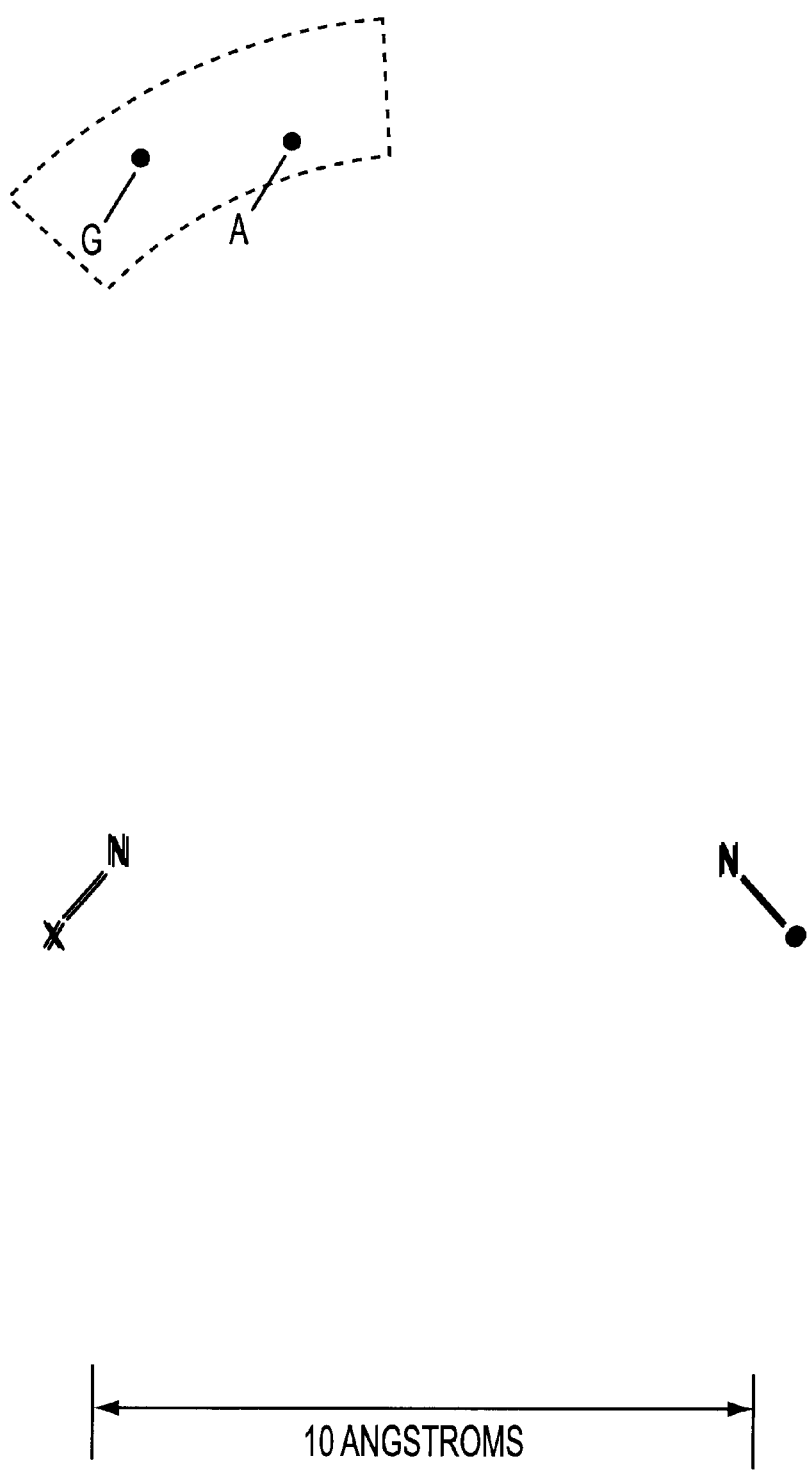
FIG. 11 is a schematic illustration, drawn to scale, summarizing the acceptable range for D-circle radius, $\Theta$ and $\zeta$ for the purine/antiparallel motif for designed residues W. The only molecular details shown are the glycosyl bonds, which are drawn with correct length and orientations. The positions of the glycosyl bonds for the canonical base-pairs RY, are denoted by "x" and "o" as in previous figures. The positions of the glycosyl bonds for the canonical third-strand bases A and G are denoted by those base letters. Note that the A and G third-strand base glycosyl bonds lie at somewhat different positions and on different circles, but have very similar orientations in this motif. The area surrounded by dots substantially encompasses the acceptable area in which the C1' end of the glycosyl bond of designed N residues can reside, derived from the acceptable ranges in Tables 4, 5 and 6.
Figure 12:
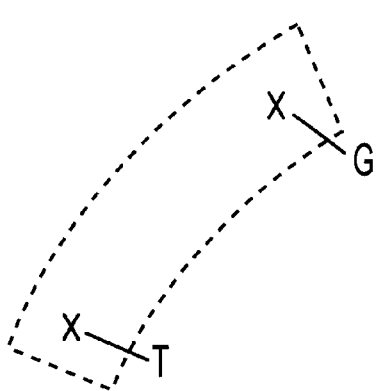
FIG. 12 is a schematic illustration, drawn to scale, summarizing the acceptable range for D-circle radius, $\Theta$ and $\zeta$ for the T and G/parallel motif for designed residues N. The only molecular details shown are the glycosyl bonds, which are drawn with correct length and orientations. The positions of the glycosyl bonds for the canonical base-pairs RY, are denoted by "x" and "o" as in previous figures. The positions of the glycosyl bonds for the canonical third-strand bases T and G are denoted by those base letters. Note that the T and G third-strand base glycosyl bonds lie at substantially different positions but on substantially the same D-circles, and with similar orientations in this motif. The area surrounded by dots substantially encompasses the acceptable area in which the C1' end of the glycosyl bond of the designed N residues can reside, derived from the acceptable ranges in Tables 4, 5 and 6.
Figure 12:
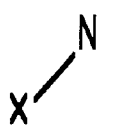
Figure 12:
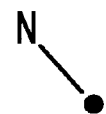
Figure 12:
Figure 13:
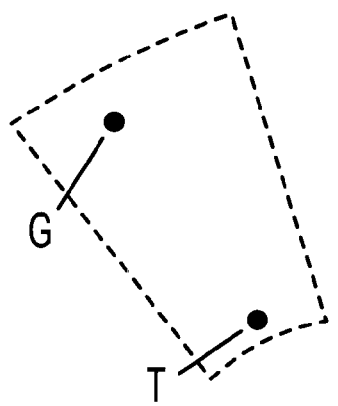
FIG. 13 is a schematic illustration, drawn to scale, summarizing the acceptable range for D-circle radius, $\Theta$ and $\zeta$ for the T and G/antiparallel motif for designed residues N. The only molecular details shown are the glycosyl bonds, which are drawn with correct length and orientations. The positions of the glycosyl bonds for the canonical base-pairs RY, are denoted by "x" and "o" as in previous figures. The positions of the glycosyl bonds for the canonical third-strand bases T and G are denoted by those base letters. Note that the T and G third-strand base glycosyl bonds lie at substantially the same position and with similar orientations, but on substantially different D-circles in this motif. The area surrounded by dots substantially encompasses the acceptable area in which the C1' end of the glycosyl bond of the designed N residues can reside, derived from the acceptable ranges in Tables 4, 5 and 6.
Figure 13:
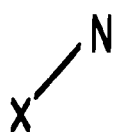
Figure 13:

An inverted base pair is formally defined and obtained by rotating by 180° the H-bonded complementary base pair RY about the axis that is the perpendicular bisector of the line between the $C_1{'}$ ends of the two glycosyl bonds. The inverted AT and GC base pairs resulting from the rotation process, which are therefore TA and CG, are illustrated in FIG. 8. With this definition, the base pairs retain their geometry as required, but the pyrimidine base now resides on the designated center or core strand, which provides a base-pair target for designed residues N for triplexes with mixed purine-pyrimdine sequences in the center strand. As before, these inverted base-pair targets are denoted as YR, and resulting triplets as N:YR.

The terms direct and inverted base pair are used to emphasize that the designed residues often bind to both bases in the target base pair, not just the center-strand base. Indeed, in the invention, residues designed to bind to inverted base pairs must bind to both bases in the duplex, since the target pyrimidine base has only one H-bonding site in the major groove, whereas a minimum of two such H-bonds are needed to achieve sufficient binding affinity.

Design of N Residues

The present invention utilizes the fact that both the canonical AT/U and GC direct base-pairs and their inverted counterparts in standard A- or B-type duplexes have known, substantially-identical stereochemistry regarding glycosyl-bond location and orientation, and are substantially coplanar. Moreover, the designed third-strand residues form base triplets that are also substantially coplanar. Substantially coplanar includes the propeller twist of the base pairs that does not affect the two-dimensional modelling described below. These unusual and advantageous stereochemical conditions enable the creation of novel residues that when incorporated into third strands can stably or specifically bind to direct and inverted target base pairs. The novel residues are designed to form triplets that are mutually conformable with base triplets formed with direct base pairs. This means that third strands can be designed to bind stably and specifically to target duplexes with strands of mixed purine and pyrimidine sequences, and therefore to substantially any sequence. The two-dimensional rules and guidelines for such design purposes are easy to visualize and implement, compared to the complex design required in three dimensions. Furthermore, the rules and guidelines define families of compositions of matter (residue families), and within the families, the rules and guidelines define particular compositions of matter (residues) either novel or previously reported in the literature.

In the invention, "rules" are design principles that must be followed; and if violated, the residue under consideration when incorporated in the third strand may not bind stably or specifically to its target inverted or direct base pair. "Guidelines" are design concepts that, if followed, allow for the design and inclusion of residues that stably and/or specifically bind to its target direct or inverted base pair. However, it may be possible to design third-strand residues if one or more of the guidelines are not conformed to, although the resulting triplex is expected to be less stable.

The complete design process proceeds as follows: (1) Choose the third-strand binding motif (Table 2) for which the residue is to be designed. (2) Determine the planar molecular framework to which hydrogen bonding substituents or functional groups are to be added in conformity with the two-dimensional rules and guidelines for that motif. (3) Complete the design either by database searching for molecules with the desired molecular framework and appropriate functional groups or by constructing a novel residue with the desired molecular framework and appropriate functional groups. (4) Confirm the design using two-dimensional and three-dimensional space-filling models and energy minimization techniques. In this design process, three-dimensional space-filling modelling is used only to confirm a design, a much simpler use of 3D modelling than de novo design. (5) Synthesize the residue and incorporate into a third-strand oligonucleotide to quantify its stability and specificity in the appropriate triplex test system for that motif.

The rules and guidelines exploit the notion that what is known to work with canonical-base third strands will work with designed-residue third strands; that is, the stereochemistry applicable to the base triplets formed with canonical direct base pairs and third strand canonical bases can be used to deduce novel third-strand residues appropriate to forming mutually conformable base-triplets with the inverted base pairs.

In designing residues N in the practice of the invention using the two-dimensional rules and guidelines of Table 3, the following procedure is useful: (1) devise a planar candidate residue, $N_c$, with at least two H-bond donors/acceptors; (2) place H-bond donor/acceptors of $N_c$ at their preferred distance (see Table 7) to form triplets $N_c$:RY or $N_c$:YR; then (3) $N_c$ is deemed acceptable for that motif if at least one (preferably two) of the two H-bonds is a standard substantially-linear bond (with the vector from the donor atom to the hydrogen atom deviating no more than 25° from the vector pointing from the donor to the acceptor atom), and if the glycosyl bond position and orientation of $N_c$ is acceptable; (4) $N_c$ is further confirmed as an acceptable residue by three-dimensional space-filling modelling and energy minimization techniques.

It is important to recognize that while the foregoing process was developed for the natural ribose and deoxyribose phosphate backbones, in fact the invention applies to any and all unnatural or synthetic third-strand backbones that do not disturb target base-pair stereochemistry, and yet have sufficient backbone entropic constraints.

TABLE 3

| Design Process Element | Rule/Guideline |
| --- | --- |
| Duplex Conservation. The distance between the origins of and the directions of the glycosyl bonds of the target base pair RY in the triplet Z:RY, N:YR, and N:RY must be substantially the same as that in A-and B-type duplexes, which are the same. | Rule |
| Glycosyl bond correspondence. For a triplet N:RY or N:YR in a specified motif, the tip of the glycosyl bond vector for each residue W should lie substantially on or between the imaginary D-circles and substantially in the same positions as those defined by the canonical base triplets Z:RY for that motif. | Guideline |
| Glycosyl bond direction. For a triplet N:RY or N:YR in a specified motif, the glycosyl vector for each residue N preferably points substantially outward from the unique circles, or if tangential, toward empty space in the circles for that motif. | Guideline |
| Framework planarity. The molecular framework for N should be substantially planar. | Guideline |
| Chemical group restriction. The chemical groups adorning the framework of N should be able to lie in the same plane as the framework or substantially no more distant from the plane than those of the canonical bases. | Guideline |
| Duplex Hydrogen-bonding (H-bonding) target. The H-bonding target for N is either an R base or both bases of the direct base pair RY, and must be both bases of the inverted base pair YR. | Rule |
| Number of H-bonds. N must form at least two | Rule |

TABLE 3-continued

| Design Process Element | Rule/ Guideline |
|---|---|
| H-bonds with the target base RY or YR base pair. | |
| Water-mediated H-bonds. H-bonds between N and RY or YR may be direct or mediated by no more than one $H_2O$ molecule. | Rule |
| Nonstandard H-bonds. H-bonds between N and RY or YR may include non-standard and non-linear H-bonds, but at least one and preferably two, standard substantially-linear H-bonds must be present. | Rule |

Duplex Conservation

The salient features regarding the rule of duplex conservation are:

1. In all triplex motifs, the H-bonding schemes for the target direct base pairs RY and the inverted base pairs YR are exactly as they occur in A, B, C, D and Z DNA. This results in the $C_1'$ sugar atoms of the two members of the four possible base pairs AT, TA, GC and CG all having essentially the same separation distance, which is between 10.8–11.3 Å.
2. While it was earlier thought that in at least some triplex motifs, the core target duplex exists in the A-type duplex form, some evidence has recently emerged that the core duplex in at least some triplex motifs may be of the B-type or somewhere between the two. However, helix form only affects the way the backbone strands wind about each other and base pairs tilt and overlap; but it has no apparent impact on the H-bonding schemes and stereochemisty of the target base pairs themselves, or on the H-bonding schemes of the base triplets of triplexes (see 4. below).
3. In all triplex motifs, the third strand, regardless of its orientation (parallel or antiparallel) with respect to the purine-rich strand of the target duplex, lies in the major groove of the target duplex. Moreover, the ribose-phosphate backbone of the third strand has a sufficient number of rotatable bonds in each residue to adjust to the H-bonding requirements of each of the observed triplex motifs.
4. In the major groove of the core target duplex, the residues Z or N can H-bond, depending on the triplex motif (and the structure of N), either only to $N_7$ and the $C_6$ substituent of the purine member of a direct target base pair; or to either or both these sites and to the $C_6$ substituent of the pyrimidine member of such a pair. Further, Z or N can H-bond to the $C_4$ substituent of the pyrimidine member of an inverted target base pair and at least to the $C_6$ substituent of the purine member of the target pair.

Glycosyl Bond Correspondence

For purposes of the present invention, a glycosyl bond is defined in its broadest aspect to be the bond between a base or residue and a backbone. To illustrate, in the case of the canonical bases and native sugar-phosphate backbones, the glycosyl bond is the bond between the C1' sugar atom and either the N9 purine or N1 pyrimidine atoms. In the case of a residue with a native backbone, it is the bond linking the C1' sugar atom to the residue. In the case of a residue with other than a native backbone, it is the bond between the residue and the backbone.

For a triplet N:RY or N:YR in a specified motif, the sugar $C_1'$ end of the glycosyl bond for each residue N designed by the rules and guidelines of this invention (designed residue) should lie substantially on or between the unique circles and substantially in the same relative positions as those defined for the third-strand residues by the canonical base triplets Z:RY for that motif (defined quantitatively in Tables 5 and 6). Ideally, both canonical base triplets should have substantially the same D-circle center and radius, as is the case in the pyrimidine/parallel and in the purine/parallel motifs (see FIGS. 2 and 3). In the other motifs, the two canonical base triplets lie on D circles of somewhat different centers and radii.

By a well-known principle of plane geometry, the three points located at the $C_1'$ ends of the three glycosyl bonds lie on the circumference of a unique circle, that is, the D circle of the invention. The center of the D circle is located at the intersection of the perpendicular bisectors of any two of the three lines connecting the three C1' points.

Figure 7:
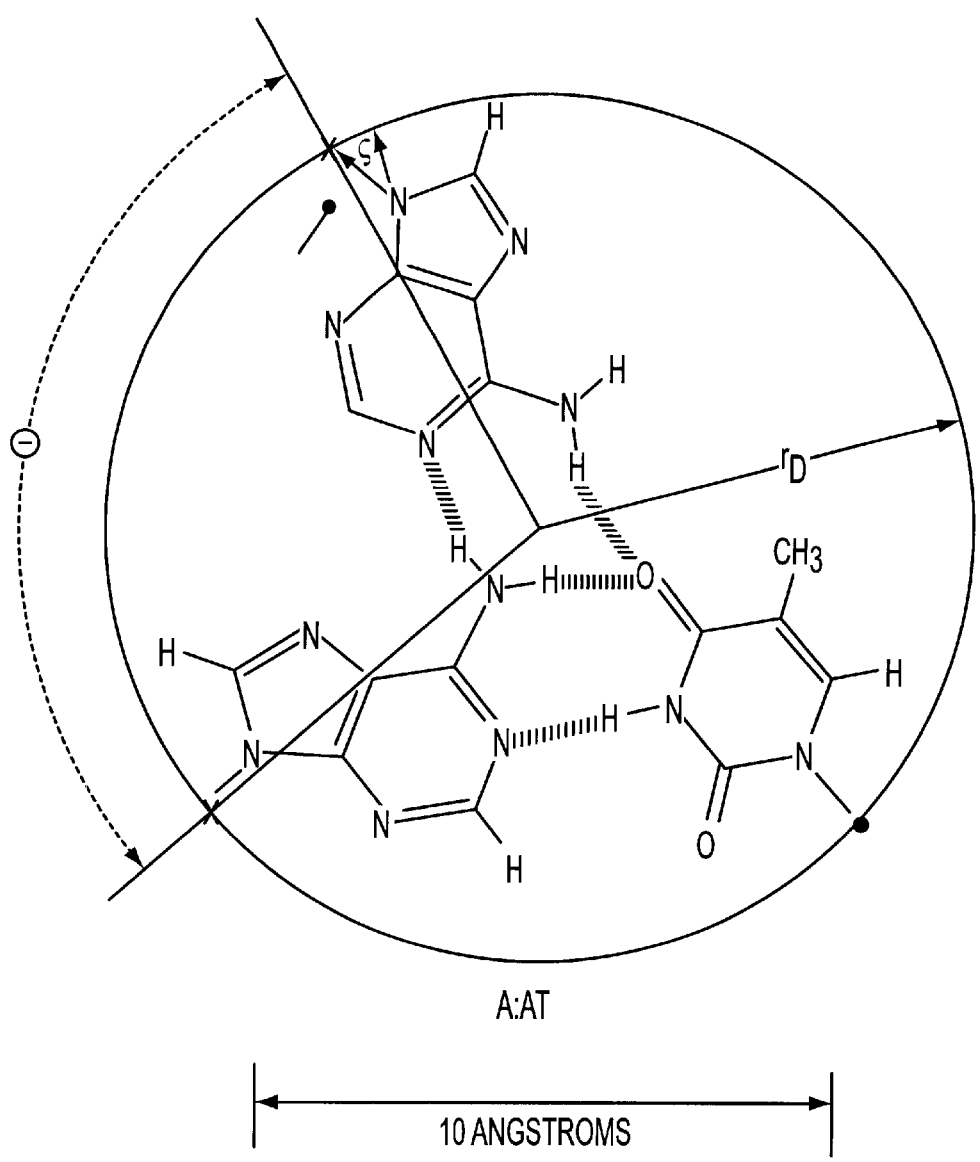

The H-bonding patterns and the D circles for all triplets of canonical base pairs for the five motifs of Table 2 are shown in FIGS. 2–6, and the radius of the D circle for each canonical base triplet is summarized in Table 4 below, along with the acceptable and preferred range of values for D-circle radius for designed residues N. In FIG. 7, the definition of D-circle radius is illustrated schematically (as are also the definitions of the location and orientation parameters $\Theta$ and $\zeta$ for the glycosyl bonds of the third strand base).

TABLE 4

| | D-Circle Radius Values (Å) | | |
|---|---|---|---|
| Motif | Canonical | Triplet Z:RY | Range for N:RY or N:YR Acceptable \| Preferred |
| Pyrimidine/ parallel | T:AT (8.0 ± 0.4) | C:GC (7.8 ± 0.4) | 7.0–8.6 \| 7.4–8.4 |
| Purine/ parallel | A:AT (7.4 ± 0.4) | G:GC (7.8 ± 0.4) | 6.7–8.6 \| 7.0–8.2 |
| Purine/ antiparallel | A:AT (7.2 ± 0.4) | G:GC (7.6 ± 0.4) | 6.5–8.6 \| 6.8–8.0 |
| T and G/ parallel | T:AT (8.0 ± 0.4) | G:GC (7.8 ± 0.4) | 7.0–8.6 \| 7.4–8.4 |
| T and G/ antiparallel | T:AT (6.4 ± 0.3) | G:GC (7.6 ± 0.4) | 5.9–8.2 \| 6.2–7.8 |

In Table 4, the ± ranges for the canonical base triplets are determined from the deviations tolerated in canonical duplexes and triplexes, including modelling experimental error. The acceptable ranges were determined by evaluating ranges allowable in the five known motifs, and performing two-dimensional modelling with different acceptable H-bond distances and angles, so as to avoid steric hindrance and strain in the backbone. The preferred ranges were picked to be close to the canonical base triplets.

Table 5 below presents the clockwise angular displacement values $\Theta$ (on the D circle) of the C1' atom attached to the z base from the purine (R) C1' sugar atom of a direct target base pair RY in a canonical triplet Z:RY in each motif (see FIG. 7). (For inverted base pairs, $\Theta$ is measured clockwise from the pyrimidine base Y that resides in precisely the same position in the models as the purine base of a direct base pair, see below). The $\Theta$ values were determined from two-dimensional modelling as represented in FIGS. 2–6.

TABLE 5

Θ value

| Motif | Canonical | Triplet Z:RY | Range for N:RY or N:YR Acceptable \| Preferred |
|---|---|---|---|
| Pyrimidine/ parallel | T:AT (67° ± 3°) | C:GC (66° ± 3°) | 53–82° \| 57–77° |
| Purine/ parallel | A:AT (102° ± 5°) | G:GC (102° ± 5°) | 81–125° \| 92–112° |
| Purine/ antiparallel | A:AT (114° ± 5°) | G:GC (99° ± 5°) | 86–128° \| 92–120° |
| T and G/ parallel | T:AT (67° ± 3°) | G:GC (102° ± 5°) | 62–107° \| 64–105° |
| T and G/ antiparallel | T:AT (97° ± 5°) | G:GC (97° ± 5°) | 90–110° \| 90–106° |

In Table 5, the ± ranges for the canonical base triplets were determined from the deviations tolerated in canonical duplexes and triplexes, including modelling experimental error. The acceptable ranges for N residues were determined by evaluating ranges allowable in the five known motifs, and performing two-dimensional modelling with different acceptable H-bond distances and angles so as to avoid steric hindrance and severe strain in the backbone. The preferred ranges were picked to be close to the canonical base triplets.

Glycosyl Bond Direction

Figure 1:
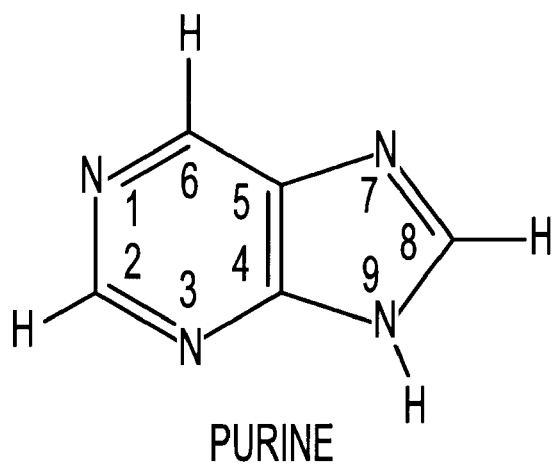
FIG. 1 depicts the standard ring numbering scheme for purines and pyrimdines.
Figure 1:
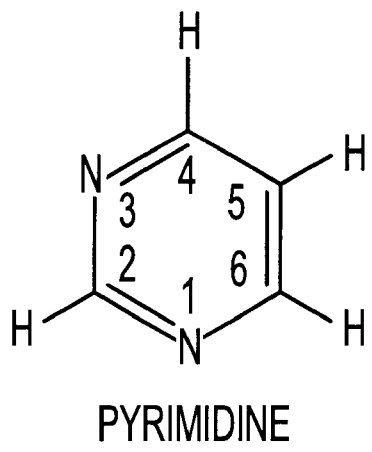
Figure 1:

For a triplet N:RY or N:YR in a specified motif, the glycosyl bond for each residue N should either point substantially outward from or substantially tangential to the D-circle. If substantially tangential, it should point toward the empty space in the D-circle to eliminate the possibility of steric interference between backbone atoms and base-triplet atoms of neighboring triplets. The glycosyl bond direction is that pointing from the $N_9$ atom of the purine base to the $C_1'$ atom of the sugar, or from the $N_1$ atom of the pyrimidine base to the $C_1'$ atom of the sugar. In FIGS. 2–6, the $N_9$ and $N_1$ atoms are denoted only as N (for nitrogen) to preserve the geometrically accurate two-dimensional representation. FIG. 1 illustrates the usual numbering scheme for purines and pyrimdines.

Direction is quantified by the parameter, ζ, which is the angle (measured clockwise) formed between the D-circle radius and the glycosyl bond vector of the Z or N third-strand residue (see FIG. 7). The ζ angles may be observed in FIGS. 2–6, and the values and ranges are presented in Table 6 below. The preferred range of values are substantially the same as those for the canonical base triplets, Z:RY, but acceptable values include all outward pointing glycosyl bonds (low values of ζ) to values tangential to the circle (values of ζ near +90° or −90°) provided there is no steric hindrance.

TABLE 6

| Motif | ζ value Canonical | Triplet Z:RY | Range for N:RY or N:YR Acceptable \| Preferred |
|---|---|---|---|
| Pyrimidine/ parallel | T:AT (0° ± 5°) | C:GC (0° ± 5°) | −90 to +90°\| −30 to +30° |
| Purine/ parallel | A:AT (−26° ± 5°) | G:GC (−21° ± 5°) | −100 to +60°\| −50 to +15° |
| Purine/ | A:AT | G:GC | −45 to +120°\| |

TABLE 6-continued

| Motif | ζ value Canonical | Triplet Z:RY | Range for N:RY or N:YR Acceptable \| Preferred |
|---|---|---|---|
| antiparallel | (51° ± 5°) | (67° ± 5°) | 0 to 90° |
| T and G/ parallel | T:AT (0° ± 5°) | G:GC (−21° ± 5°) | −90 to +90°\| −30 to +30° |
| T and G/ antiparallel | T:AT (76° ± 5°) | G:GC (67° ± 5°) | −30 to +120°\| 0 to 90° |

In Table 6, the ζ ranges for the canonical base triplets take account of the deviations tolerable in canonical duplexes and triplexes and also the experimental error of modelling. The preferred ranges are those nearer the values for the canonical third-strand bases. The acceptable ranges include the preferred ranges plus essentially any angle that will not cause steric hindrance between the backbone and the third-strand residues.

Stable triplex formation will occur when: a) the third-strand residue N of a base triplet is H-bonded optimally to the direct or inverted base pair; b) the glycosyl bond has a radius in the preferred or acceptable range (Table 4) and has a preferred or acceptable position (Table 5); c) its glycosyl bond direction is in the preferred or acceptable range (Table 6); and d) the other rules and guidelines are adhered to. If the direction of the glycosyl bond of the designed N residue is outside the acceptable range for that motif, triplex formation is unlikely.

Framework Design and Planarity

The molecular framework for N should be substantially planar and sterically compatible with the van der Waals thickness of one base pair in a nucleic acid helix; i.e., about 3.4 Å. The dimensions of the framework and the location of H-bond donor and acceptor substituents must allow H-bond formation with the direct or inverted base-pair targets. At the same time, the D-circle radius on which the glycosyl bond of N lies should fall within the preferred or acceptable ranges defined in Table 4; and that glycosyl bond should fall within the range of positions and orientations defined in Tables 5 and 6 for the various motifs.

The range of values for the D-circle radius, and the angles Θ and ζ that locate and orient the glycosyl bonds of the designed residue for each motif are quantified in Tables 4, 5 and 6; and the combined acceptable ranges are illustrated schematically as areas in FIGS. 9–13. These figures are convenient for showing whether the glycosyl-bonds of a designed residue N meets the guidelines of the invention, and will be used for that purpose in the Examples provided below.

While many types of heterocyclic and nonheterocyclic molecular structures, all within the scope of the invention, can be devised, modelled, and synthesized that fulfill the framework, glycosyl-bond location, and H-bonding requirements, carbon-nitrogen heterocycle frameworks are, a priori, the simplest choices. Novel carbon-nitrogen heterocycle frameworks with two, three and four rings that provide aromaticity and structural planarity, rigidity, and molecular dimensions compatible with preferred D-circle sizes, are preferred compositions of matter in the invention. These two, three and four ring frameworks are preferred also because they provide a number of ring nitrogens to serve as H-bond donors, acceptors, a number of positions for N—$C_1'$ glycosyl bonds, and reactive ring atoms to which hydrogen-bonding donor and acceptor functional groups (or functional groups capable of other weak interactions) may be attached.

Figure 14:
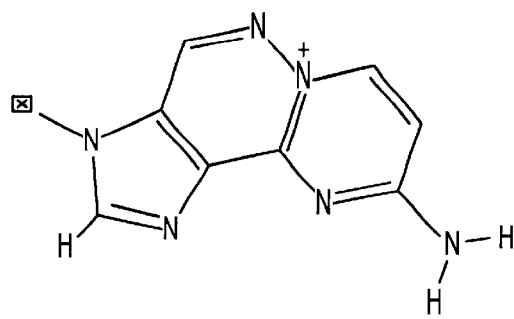
FIG. 14 depicts two three-ring carbon-nitrogen heterocycles, one four-ring carbon-nitrogen heterocycle, and one two-ring carbon-nitrogen heterocycle as examples of suitable residues according to the present invention, drawn to scale.
Figure 14:
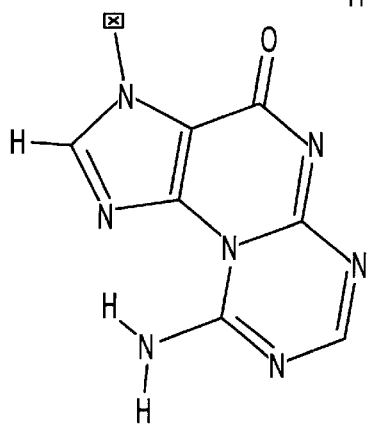
Figure 14:
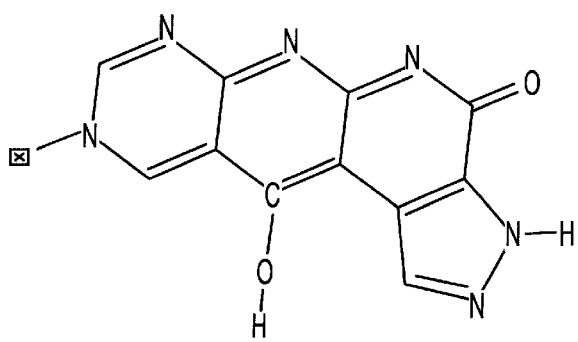
Figure 14:
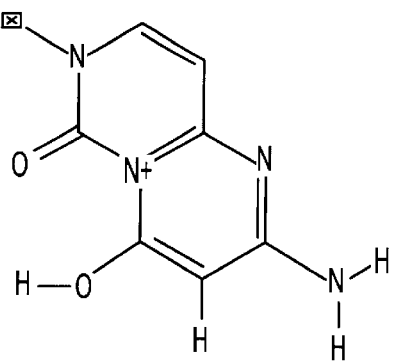

Two examples of such three ring heterocycles, one of a four-ring heterocycle, and one of a two-ring heterocycle are shown in FIG. 14. Many ring carbons and ring nitrogens are potential sites for functional H-bonding substituents such as carbonyl (C=O), hydroxyl (—OH) or amino (—NH$_2$) groups, as are unsubstituted ring nitrogens as well as any other group capable of serving as H-bond donors or acceptors or entering into other weak interactions. The ring positions of the functional groups may be other than those shown in the three specific examples of the figure. These novel frameworks are designated "F" to differentiate them from the wide range of frameworks and residues N that are within the scope of the invention. Specific compositions of matter based on the framework (F-residues) will be denoted by F1, F2, F3, F4, etc. below. The three and four ring heterocycle F frameworks and F-residues are preferred embodiments of the invention. These include the carbon-nitrogen ring heterocycles in the Examples and may also include rings containing other atoms such as O, S, etc.

Chemical Group Restriction and Design

The chemical groups (here usually called functional groups, or substituents) adorning the framework of N should lie (or be able to lie) preferably in the same plane as the framework or substantially no more distant from the plane than those of the canonical bases. The standard H-bonds listed with their preferred bond distances in Table 7 below are the preferred functional groups in the invention, although other sources of H-bond acceptors such as fluorine atoms are known that can be substituted on the framework (L. Pauling, *Nature of the Chemical Bond, Cornell* University Press, 3rd ed., p. 454 (1960)). Also, it is recognized that certain complementarily-sized hydrophobic substituents on the framework can also provide binding energy alternatives to that provided by H-bonding. When bound to ring atoms of heterocycles, some H-bonding substituents conform to the planar restriction (in some cases, when rotated about their single bonds into positions compatible to H-bonding within the plane). Also, in some cases, an H-bond donor can rotate its substituent to direct its donor H-atom to an acceptor in the nearest-neighbor base pair above or below the opposing target base pair.

Table 7 below presents standard H-bonding functional groups and the H-bonds they form. The ± values indicate the typical range, and therefore the preferred range, of distances from the center of the donor atom of the H atom to the center of the acceptor atom.

TABLE 7

| H-bond | Approximate bond length, Å |
|---|---|
| O—H—O | 2.70 ± .10 |
| O—H—O$^-$ | 2.63 ± .10 |
| O—H—N | 2.88 ± .13 |
| N—H—O | 3.04 ± .13 |
| N$^{30}$—H—O | 2.93 ± .10 |
| N—H—N | 3.10 ± .4 |

Duplex H-bonding Target and Design of H-bonds

In the case of a direct base pair RY, the H-bonding target for N is either the R base or both bases. N must form at least two H-bonds with a target RY or YR base pair if other substantial weak interactions between the base pair and the N residue are not present. For inverted base-pairs, the N residue must bind to both bases in the pair since only one H-bonding site is available on the Y base (see FIG. 8). Otherwise, the glycosyl bond D-circle, position and direction guidelines will not be met.

As in complementary double helical nucleic acids (e.g., DNA, RNA duplex genomes), molecular interaction through H-bonding is the primary force driving specific triplex formation. Third strand pyrimidine residues H-bond to N$_7$ and the C$_6$ substituent on purine residues of a purine-rich duplex strand, which explains why purine-rich tracts located on one strand of the core duplex are required for triplex formation. From the established third strand binding code (Table 1), it is apparent that neither pyrimidine nor purine oligonucleotides bind to duplex targets of sequences containing a substantial mix of purines and pyrimidines in each strand. This is because optimal H-bonding schemes for the triplets, i.e. those which conform to the glycosyl-bond-related guidelines governing triplex formation, require that the third strand residues H-bond to both N$_7$ and the C$_6$ substituent on the purine residues of the purine-rich strand.

Hydrogen bonds are mainly electrostatic in nature. Compared with covalent bonds of well-defined length, strength and orientation, hydrogen bonds are "soft" and only weakly directional (Saenger, W., in *Principles of Nucleic Acid Structure*, Springer-Verlag New York Inc. (1984)). Three novel types of H-bonds, along with conventional ones, have been recognized in nucleic acid and nucleoprotein interactions: the carbon donor CH . . . O and CH . . . N H-bonds (Taylor and Kennard, *JACS* 104: 5063 (1982)); the water-bridged hydrogen bond (Letai, et al., *Biochemistry* 27: 9108 (1988); Cruse, et al., *Proc. Natl. Acad. Sci. USA*, 91, 4160 (1994)); and the "three centered" system, in which two acceptors compete for the same H-atom, forming a bifurcated, relatively long, weak hydrogen bond (J. Donohue, Selected topics in hydrogen bonding. *In: Structural Chemistry and Molecular Biology* (Rich and Davision, Eds.), 443, Freeman, San Francisco, (1968)); Jeffery and Takagi, *Acc. Chem. Res.* 11: 264 (1978)). In the invention, both conventional and non-standard H-bonds are considered in deducing possible H-bonding schemes with at least two H-bonds between a third strand base or residue and a direct or inverted base pair. Also, fluorine substituents on frameworks are considered as acceptors for donated H atoms (L. Pauling, *Nature of the Chemical Bond*, Cornell University press, 3rd ed., p. 454 (1960)).

According to the present invention: (1) H-bonds between N and RY or YR may be mediated by no more than one H$_2$O molecule; and (2) H-bonds between N and RY or YR may include non-standard and non-linear H-bonds, but at least one standard, linear H-bond must be present. Less than 25° bending from linearity is considered linear in the practice of the invention, that is, will form a strong H-bond. Non-standard H-bonds in place of one of the two desired H-bonds, such as those involving carbon-hydrogens, e.g., CH . . . N, CH . . . O, CH$_3$ . . . N, CH$_3$ . . . O are not to be discounted.

Specificity of H-bonding to Inverted Base Pairs

Specificity of triplet formation is determined by the H-bond donor and acceptor locations and patterns. There are situations where residues designed to bind specifically to a one inverted base pair (TA or CG) may also bind to one of the direct base pairs (GC or AT). The purpose of this discussion is to describe the situations and to demonstrate that this reduced specificity does not affect the utility of the invention in important applications.

For the inverted base pair TA, there are three potential standard H-bonding sites for triplet formation that are from left to right in FIG. 8: the thymine $C_4$=O acceptor, the adenine $C_6$—$NH_2$ donor and the adenine ring $N_7$ acceptor. We number and denote the acceptor and donor pattern for these three sites as follows:

| 1 | 2 | 3 |
|---|---|---|
| acc. | don. | acc. |

To preserve the stereochemical meaning of the numbering scheme (see below), the thymine $C_5$—$CH_3$ non-H-bonding position, which we denote as "non" must also be considered. Thus, we have as the following left-to-right pattern for these four sites:

| 0 | 1 | 2 | 3 |
|---|---|---|---|
| non. | acc. | don. | acc. |

Figure 2:
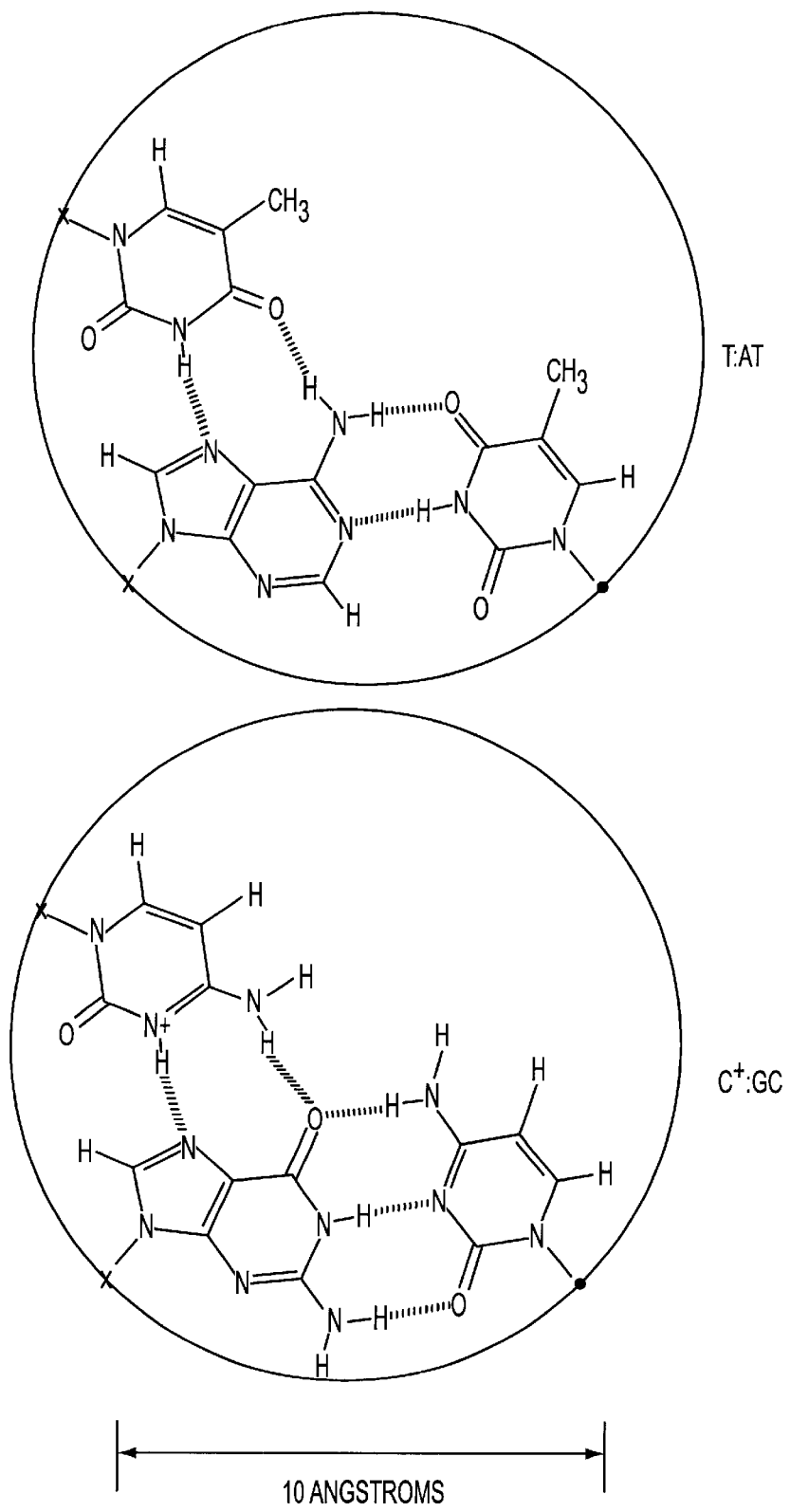
FIG. 2 is a two-dimensional illustration, drawn to scale, of base triplet hydrogen bonding (H-bonding), imaginary D-circle centers and radii for canonical pyrimidine/parallel motif base triplets T:AT and $C^+$:GC. All H-bonds to the target direct base pair were placed at standard distances (Table 7) and are essentially linear (well within the 25° preferred bending limit from linearity). The D-circle radii for both T:AT and $C^+$:GC triplets, 8.0 Å and 7.8 Å, respectively, are substantially the same, as are the positions ($\Theta$=67° and 66°, respectively) and orientations ($\zeta$=0° for both) of the third-strand base glycosyl bonds. The "x" and "o" symbols at the ends of the glycosyl bonds denote parallel and antiparallel backbone directions, respectively. The figure therefore shows that the backbone of the third strand base is parallel to the backbone of the purine base of the target base pair. Model drawing errors are estimated to be about 3% of measured distances.
Figure 3:
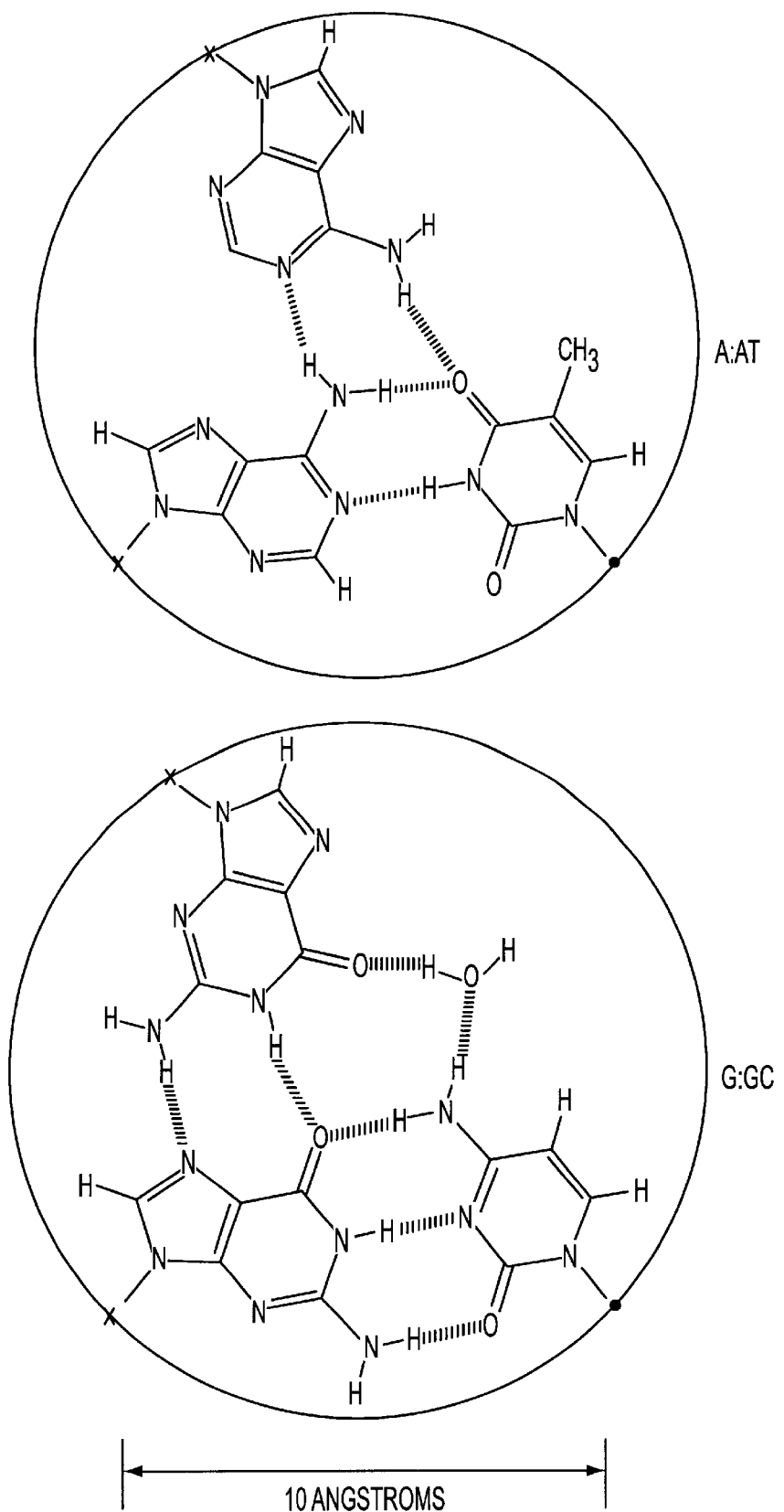
FIG. 3 is a two-dimensional illustration drawn to scale of base triplet H-bonding, D-circle centers and radii for canonical purine/parallel motif base triplets A:AT and G:GC. For each third-strand base, two H-bonds to the target direct base pair were placed at standard distances (Table 7) and are essentially linear or well within the 25° preferred bending limit from linearity. In the G:GC triplet, the H-bond involving $C_6$=O of the third-strand G base is slightly shorter than preferred (2.53 Å) but acceptable, and the H-bond involving $C_6$=O of the duplex G is slightly longer than preferred (3.26 Å) but acceptable. The D-circle radii for A:AT and G:GC triplets are slightly different, 7.4 and 7.8 Å, respectively; and the positions, $\Theta$=102° for both are substantially the same, as are the orientations $\zeta$=−26° and −21°, respectively, of the third-strand base glycosyl bond. The G:GC triplet requires an intermediary $H_2O$ molecule both to form the triplet and to achieve preferred substantially identical glycosyl-bond position and orientation for both triplets. The "x" and "o" symbols at the ends of the glycosyl bonds denote parallel and antiparallel backbone directions, respectively. Model drawing errors are estimated to be about 3% of measured distances.
Figure 4:
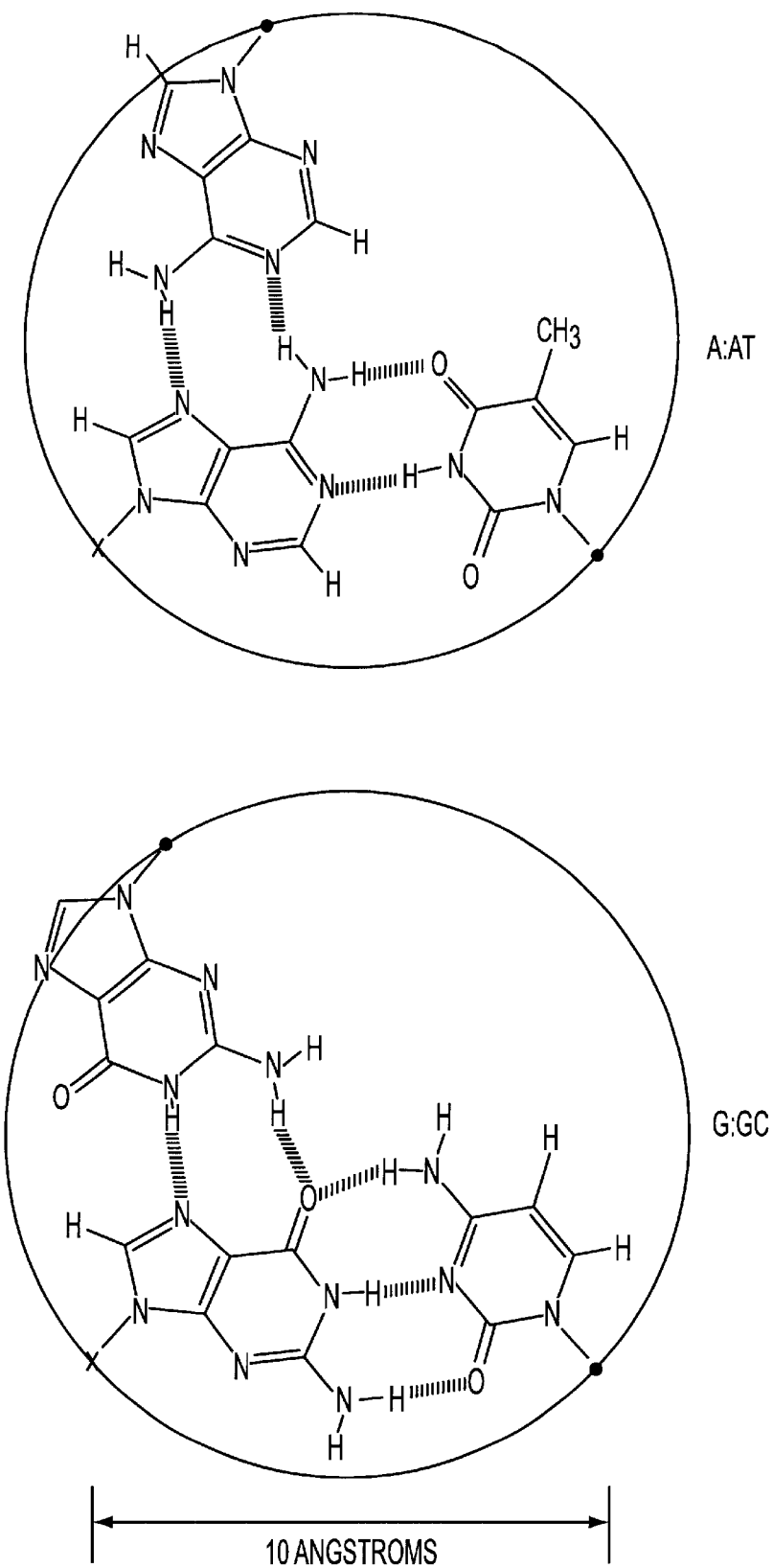
FIG. 4 is a two-dimensional illustration, drawn to scale, of base triplet H-bonding, D-circle centers and radii for canonical purine/antiparallel motif base triplets A:AT and G:GC. The H-bonds were placed at standard distances (Table 7), with all but one H-bond essentially linear or well within the 25° preferred bending limit from linearity. One H-bond, the N---H—N involving the $N_1$ of the third strand A base has a 25° bend, at the limit of the preferred range for bending. The D-circle radii are slightly different for the A:AT and G:GC triplets, 7.2 Å and 7.6 Å, respectively. The positions of the third-strand base glycosyl bonds are also somewhat different, $\Theta$=114° and 99° for A:AT and G:GC, respectively. The glycosyl bond orientations, $\zeta$=51° and 67°, respectively, are similar; both point outward and in the direction of the empty space (in the major groove of the helix) in the D-circles. The fact that the D-circle radii for A:AT are slightly smaller in the purine/parallel and purine/antiparallel motifs than in the pyrimidine/parallel motif allows for increased flexibility in the third-strand backbone as it twists and translates vertically to the next base triplet. This increased flexibility compensates for the difference in glycosyl bond position for the two triplets (measured by $\Theta$) in these motifs that reduces backbone flexibility as the third-strand nearest-neighbor bases change from A to G. The "x" and "o" symbols at the ends of the glycosyl bonds denote parallel and antiparallel backbone directions, respectively. Model drawing errors are estimated to be about 3% of measured distances.
Figure 5:
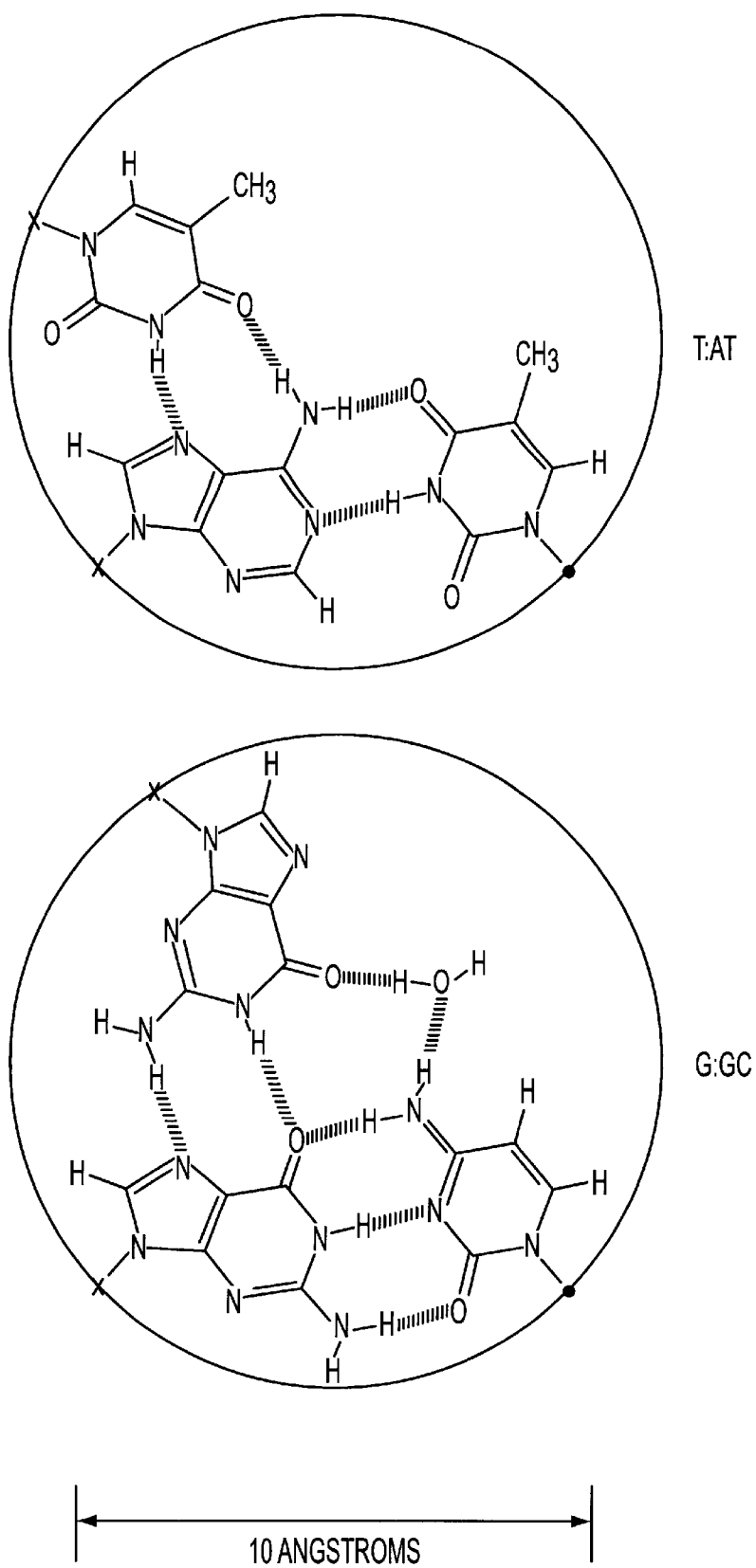
FIG. 5 is a two-dimensional illustration, drawn to scale, of base triplet H-bonding, D-circle centers and radii for canonical T and G/parallel motif base triplets T:AT and G:GC. The T:AT triplet is identical to that of FIG. 2, and the G:GC triplet is identical to that of FIG. 3. The D-circle radii are 8.0 Å and 7.8 Å for T:AT and G:GC triplets, respectively. The positions of the glycosyl bonds are quite different, $\Theta$=67° and 102° for T:AT and G:GC, respectively. The orientations of the glycosyl bonds are similar, 0° and −21° for T:AT and G:GC, respectively. The fact that the D-circle radii are large and the positions of the glycosyl bonds on the D-circles are quite different indicates there is considerable strain on the third-strand backbone for AG and GA nearest neighbors. This explains the observation that the T and G/parallel motif favors high proportions of AA and GG nearest neighbors relative to AG and GA nearest neighbors in the center or core strand. The glycosyl bond orientations are substantially outward. The "x" and "o" symbols at the ends of the glycosyl bonds denote parallel and antiparallel backbone directions, respectively. Model drawing errors are estimated to be about 3% of measured distances.
Figure 6:
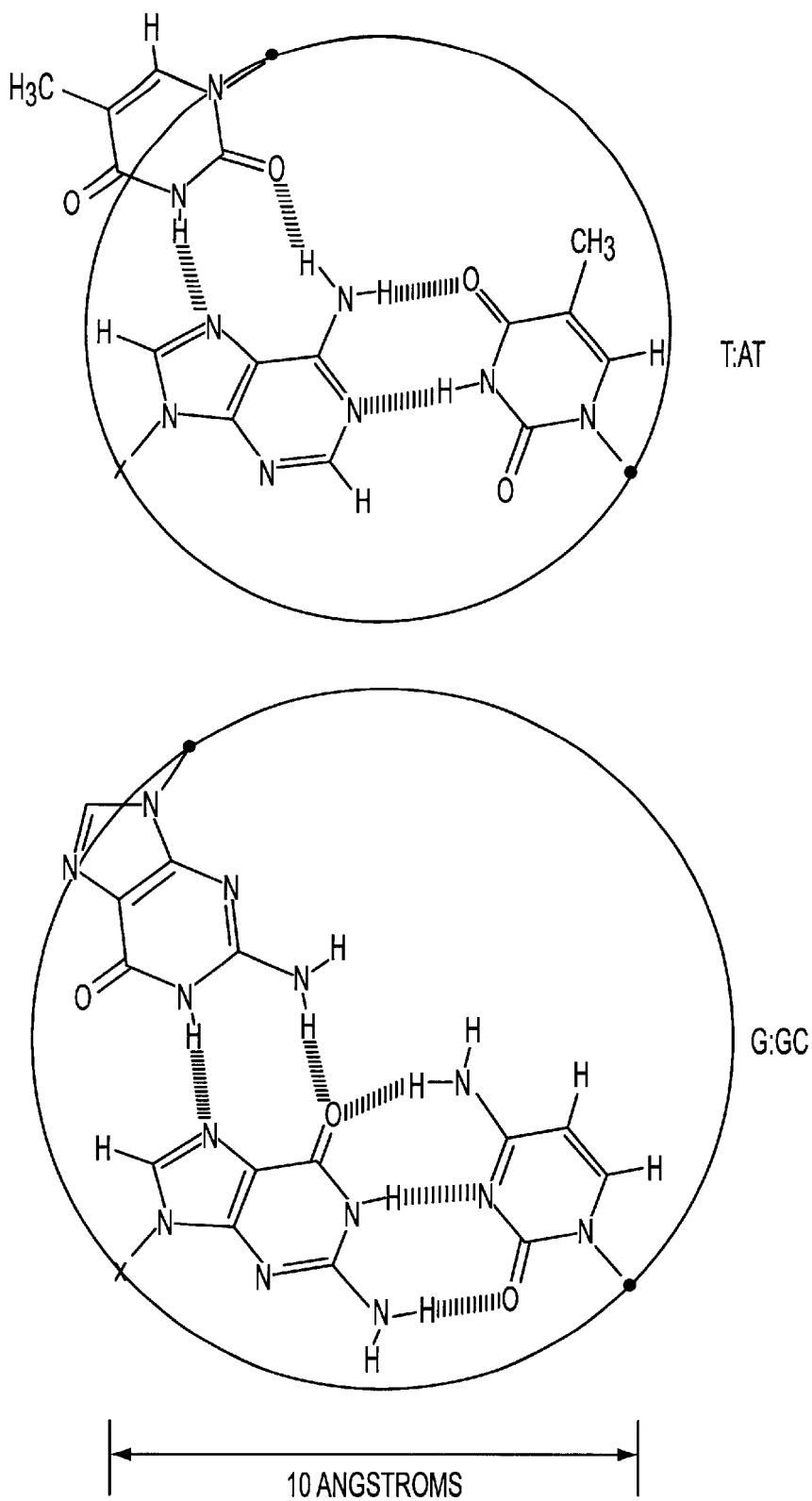
FIG. 6 is a two-dimensional illustration, drawn to scale, of base triplet H-bonding, D-circle centers and radii for canonical T and G/antiparallel motif base triplets T:AT and G:GC. The H-bonds for T:AT were placed at standard distances (Table 7), and are essentially linear, well within the 25° preferred bending limit from linearity. The G:GC triplet is identical to that of FIG. 3. The D-circle radius for T:AT is quite small, 6.4 Å, and quite different than that for G:GC, 7.6 Å. The positions of the third-strand base glycosyl bonds are identical, $\Theta$=97°, and their orientations, $\zeta$=76° and 67° for T:AT and G:GC, respectively, are similar. The glycosyl bond orientations are similar, both pointing tangential to the D-circle and toward the empty space (in the major groove) of the D-circle. The fact that the D-circle radii are small allows for increased flexibility in the backbone as it twists and translates vertically to the next base triplet. This increased flexibility partially compensates for the large difference in D-circle radii, leading to stable triplexes in this motif. The "x" and "o" symbols at the ends of the glycosyl bonds denote parallel and antiparallel backbone directions, respectively. Model drawing errors are estimated to be about 3% of measured distances.

Similarly, for the direct GC base pair there are three potential standard-H-bonding sites for triplet formation that are from left to right in FIG. 2: the guanine ring $N_7$ acceptor, the guanine $C_6$=O acceptor, and the cytosine $C_4$—$NH_2$ donor. Along with the cytosine non-H-bonding position $C_5$—H, we have the following left-to-right pattern, where the numbering indicates similar stereochemical positions as above.

| 0 | 1 | 2 | 3 |
|---|---|---|---|
| acc. | acc. | don. | non. |

For both the inverted TA and the direct GC base pairs, the 1-acc. position and the 2-don. position lie in the same relative positions, but they are not identically located with respect to the base-pair glycosyl bonds. By the same reasoning, for both the inverted CG and the direct AT base pairs, positions 1 have a donor and positions 2 have an acceptor, so that they lie in the same relative locations with respect to the base-pair glycosyl bonds, but not at the identical locations with respect to the base pair glycosyl bonds. The consequence is that some residues designed to bind to inverted base pairs TA and CG, which are denoted as $N_{TA}$ and $N_{CG}$, respectively, could possibly show reduced specificity by binding to the direct base pairs, GC and AT, respectively, i.e., in the notation of the invention: both $N_{TA}$:TA and $N_{TA}$:GC could possibly form, and similarly for $N_{CG}$:CG and $N_{CG}$:AT. Whether designed residues utilizing H-bonding positions 1 and 2 will also bind to the direct base pairs will depend on whether its backbone location is in the acceptable ranges for the particular motif.

A designed residue that binds only to its target inverted base pair, may be said to give "full" specificity, whereas a designed residue that binds also to a direct base pair may said to give "partial" specificity. A designed residue with full specificity can bind only to one of the four target base pairs, whereas with partial specificity it can bind to two of the four target base pairs.

Ultimately, what counts is the specificity of the entire third-strand, not just the specificity of any particular third-strand residue. Assuming that a third strand of 20 bases/residues is needed for a particular application, as is the case in therapeutic mutagenesis, the question of specificity in targeting a 20 base site (to make the desired mutation at that site) may be framed mathematically as: What is the probability that a third-strand targeted to a specific sequence site of 20 base pairs with both purines and pyrimdines in the center strand (an object of the invention) will target another unwanted site, say in the human genome ($3 \times 10^9$ base pairs)? For full specificity, this probability is approximately $3 \times 10^9$ $(\frac{1}{4})^{20}$=0.003. In other words, there is little chance that another, unwanted site (in the human genome) will be targeted. In the case where one of the two designed residues, $N_{TA}$ for example, is partially specific, there will on average be 5 GC sites (out of 20 base pairs) to which $N_{TA}$ can bind. In this case, the probability that a third-strand targeted to a specific mixed base-sequence site of 20 bases in the human will target another site in the human genome is approximately $3 \times 10^9 \times (\frac{1}{4})^{15} \times (\frac{1}{2})^5 = 0.09$, which is still an acceptably small chance for mistargeting.

Since partial specificity of particular residues does not detract importantly from third-strand specificity in some applications, in this invention specificity includes both full and partial specificity.

Choice of Backbones

As noted above, the compositions of the present invention include both native and artificial backbones. Backbones that have flexibility similar to native sugar-phosphate backbones and that have been shown to allow the formation of stable duplexes or triplexes are useful in the invention. In the modelling of the present invention, the stereochemistry of base triplets and acceptable H-bonding schemes of the five experimentally-verified motifs determine acceptable backbone locations on the D-circle. These motif experiments employed native sugar-phosphate backbones.

An important consideration in determining what backbones are acceptable in the invention is flexibility. Backbones may not be too stiff or too flexible. A backbone that is too stiff may not be able to conform to acceptable ranges for $r_D$, $\Theta$ and $\zeta$. A backbone that is too flexible may undergo a large negative entropy change, leading to an unfavorable positive free-energy change, upon triplex formation. A simple, acceptable measure of flexibility is the number of rotatable backbone bonds between third-strand bases on adjacent triplets. The native sugar-phosphate backbones have six rotatable bonds (i.e., the 4'C—3'C; 3'C—O; O—P; P—O; O5'C and 5'C—4'C bonds). Other commonly used analog or mimetic backbones, for example, phosphorothioate and methylphosphonate also have six rotatable bonds, and so are preferred backbones in the invention along with the native sugar-phosphate backbones. Other backbones with one or two more or one or two less rotatable bonds than the native sugar-phosphate backbone are still acceptable in the invention, provided that they have been shown to allow formation of stable triplexes. In fact, any backbone shown to form stable triplexes is acceptable.

A defining characteristic of each third strand binding motif is the polarity of the third strand relative to the center or core strand of the target duplex. The standard definition of parallel and antiparallel refers to whether the two strands of a duplex are oriented in the same (parallel) direction, both 5' to 3', or in opposite (antiparallel) directions, 5' to 3' and 3' to 5'. In the Watson-Crick duplex, the two strands are oriented antiparallel, and the bases attached to each strand are in the anti configuration about their glycosyl bonds. Likewise, in a Watson-Crick-like duplex formed with is backbones that are close analogs of the native sugar-phosphate backbone such as phosphorothioate and methylphosphonate, the two strands run antiparallel, and the bases are attached to each strand in the anti configuration about the glycosyl bond.

For triplexes comprised of native sugar-phosphate backbones or their analogs, such as phosphorothioate and methylphosphonate, parallel or antiparallel refers to the relation of third strand orientation in the triplex relative to the purine-rich center strand (or to the designated center strand). Thus, in the present invention, for analog backbones for which strand orientation may be defined and the designed residues reside in a single configuration with respect to one of the two strand orientations, the definitions of parallel and antiparallel are the same as those for native triplexes of canonical bases. For some analog backbones within the scope of the invention, however, if either (a) strand orientation cannot be defined, or (b) if strand orientation can be defined but anti and syn configurations are substantially of the same energy and switching between configurations is kinetically allowable, or if syn and anti configurations are not definable, then the concept of parallel and antiparallel strand orientations does not apply. In such cases, each third strand base in the triplex will adopt the configuration compatible with forming the most stable H-bonds, so orientation of the strand is unimportant.

Limiting Factors in Triplex Formation i. pH Range

At the upper end, third strand binding with canonical bases and N residues would be limited by ionization of ring phenolic OH substituents adjacent to unsubstituted ring nitrogens, which generally have a $pK_a$ 9–9.5. Hence, a pH of approximately 8–8.5 generally represents an upper pH limit to third strand binding. On the acid side, ionization of unsubstituted ring nitrogens serving as hydrogen acceptors for H-bonding have pKa values near 4.5 or below, so pH values below about 5 should generally be avoided.

ii. Ionic Strength

In general, third strand binding is favored by increasing ionic strength, with 0.01 M monovalent cation at room temperature serving as a lower limit. Addition of $Mg^{2+}$ to about 5–20 mM is generally very stabilizing, as is increasing monovalent cation alone up to about 1 M. The preferred monovalent cation is sodium, which does not encourage tetraplex formation of G rich strands, as does potassium ion.

iii. Length of Third Strand

In general, increasing third strand and target duplex length is favorable to third strand binding. Triplexes with adequate stability for particular purposes can be as short as about 7–10 base triplets in length, although for purposes of gene therapy by induced mutagenesis or by suppression of gene expression or of replication, lengths of 15–25 base triplets are required to limit third strand binding to unique targets in the human and other large genomes.

iv. Adducts of Third Strands

A variety of adducts on third strands, linked to either end of the strand or to a site on a base or residue where it does not interfere with H-bonding to the target, such as intercalating agents, crosslinking agents, alkylators, specific mutagens of various types, minor groove peptide and dye binders, all can in appropriate circumstances strengthen third strand binding without reducing specificity. They can thereby enhance the utility of third strands for therapeutic, diagnostic, process control and other utilities.

v. Third Strand Motif Sequence Interruptions

While the motifs have been described by reference to the base composition of the third-strand (i.e., purine, pyrimidine or T and G), it will be understood that the third strand need not contain only those bases. According to the present invention, the frequency of determinative bases and/or base analogs plus synthetic residues is no less than five out of seven. For example, in the pyrimidine/parallel motif, there can be no more than two canonical purines in seven bases and/or analogs or N residues.

Utility of the Invention

The present invention is directed to circumventing the requirement that third strand binding targets comprise strands that are very purine-rich pyrimidine-rich duplex sequences. This achievement in no way reduces the utility of third strand binding as described in U.S. Pat. No. 5,422,251 to Fresco. Rather, it enhances the utility by making virtually all Watson-Crick or complementary duplex sequences accessible to third strand binding. Presently, less than one percent of the genomic sequences of essentially all living organisms, including viruses, bacteria, invertebrates and vertebrate organisms, including mammals and particularly humans, are accessible to third strand binding. Consequently, this invention provides the basis for a quantum leap in the utility of such binding for control of replication and gene expression in all living organisms; for inducing mutations; for the repair of mutations in vitro and in vivo; including applications resulting in gene therapy, the inhibition of infectious bacteria and viruses, the creation of phenotypic mutations; for diagnostic purposes; for isolating specific double stranded nucleic acid fragments, including chromosomes, YACS, other types of DNA particles, restriction fragments; and for the development of new types of specific third strand DNA probes for diagnostic and research purposes.

To illustrate the application of the utility of one aspect of the invention, an example is provided of the design of a third strand to the purine-rich target site present at the site of the A→T substitution mutation in β globin that causes sickle cell anemia. This example has utility as a means of specifically correcting the mutation by utilizing a third strand with a psoralen moiety covalently bound to it at the position corresponding to the A→T mutation. Psoralen damage to a T base in chromosomal DNA in eukaryotes is often misrepaired to an A base, just the change required here to revert the sickle-cell β globin gene to the normal β globin gene. This therapeutic application is the subject of copending U.S. patent application to Glazer, filed concurrently herewith.

It has been known for almost 40 years that a single mutation in the β chain of hemoglobin is sufficient to cause the sickle-shaped red cells characteristic of sickle cell anemia. At the DNA level, the normal adenine base is mutated to a thymine, which causes an amino acid replacement in hemoglobin from a negatively-charged glutamic acid to an uncharged, hydrophobic valine. The normal (Lawn, et al., *Cell*. 15: 1157 (1978)) and altered DNA sequence surrounding the mutant site (boldface) is:

```
                    gag
5'..CCTGACTCCTGAGGAGAAGTCTGCCGTTACTGCCCT..3'   (normal    (SEQ ID NO:1)

3'..GGACTGAGGACTCCTCTTCAGACGGCAATGACGGGA..5'   sequence)

gug
5'..CCTGACTCCTGTGGAGAAGTCTGCCGTTACTGCCCT..3'   (mutant    (SEQ ID NO:2)

3'..GGACTGAGGACACCTCTTCAGACGGCAATGACGGGA..-5'  sequence)
```

The codons "gag" and "gug" code for glutamic acid and valine, respectively. The underlined DNA region is the target for third-strand binding. The sequence of one putative third-strand that may bind to the target, albeit weakly because of mismatches and two strand switches, is presented below.

```
                                            (SEQ ID NO:3)
         pso
          |
3'-CCTTGCTCCT/CGGCTGTTG/TCTTCCTTTGCTTCCCT
```

In the third-strand, the "/" indicates a strand switch; bold letters indicate bases opposite mismatch sites (pyrimidines in the purine-rich target strand); and "pso" indicates the attached psoralen opposite the T mutation. The left-hand sequence (before the first strand switch) is in the pyrimidine/parallel motif; the center sequence is in the G and T/antiparallel motif; and the right-hand sequence is again in the pyrimidine/parallel motif.

Figure 15A:
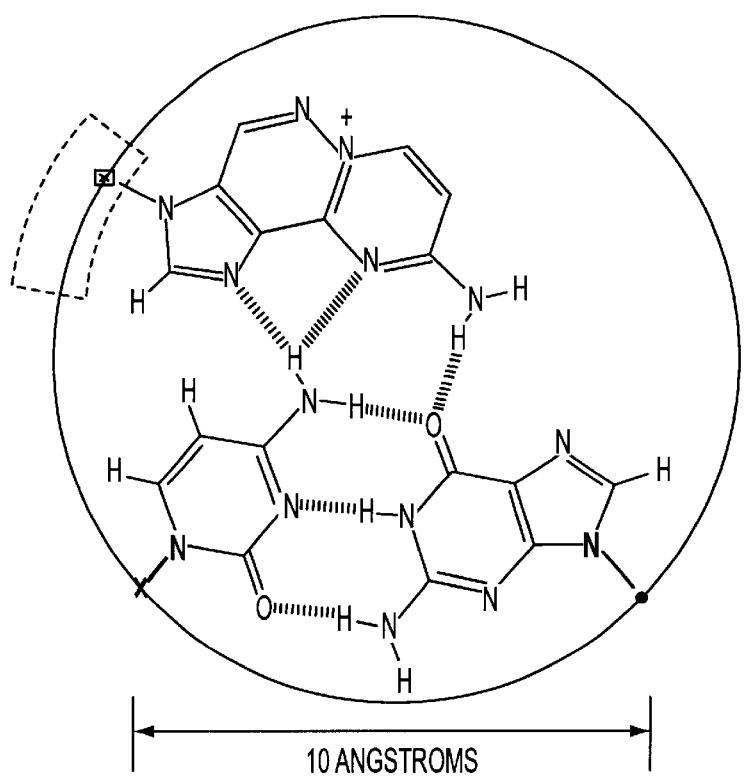
FIG. 15 depicts the designed three-ring heterocycle residue, designated Fl, that binds to the inverted CG base-pair in the pyrimidine/parallel and T and G/parallel motifs. The F1:CG triplet modelled in two-dimensions and drawn to scale superimposes on the acceptable-area diagrams for the pyrimidine/parallel (shown in FIG. 15(a)) and T and G/parallel (shown in FIG. 15(b)) motifs. The end of the F1 glycosyl bond fits well within the preferred areas for both motifs, with $r_D$=7.6 Å and $\Theta$=74°, and the orientation of the glycosyl bond, $\zeta$=–10°, is in the preferred range for both motifs. The glycosyl bond is attached to $N_9$ of F1, with F1 in the anti-configuration about the ribose. The end of the F1 glycosyl bond is denoted by a square with an x to signify that F1 may be synthesized to have its backbone either parallel or antiparallel to the center strand (with the cytosine base). Here, the parallel orientation applies. The F1 residue was positioned by placing the third-strand H-bonds at distances indicated in Table 7 for the types of H-bond involved.
Figure 15B:
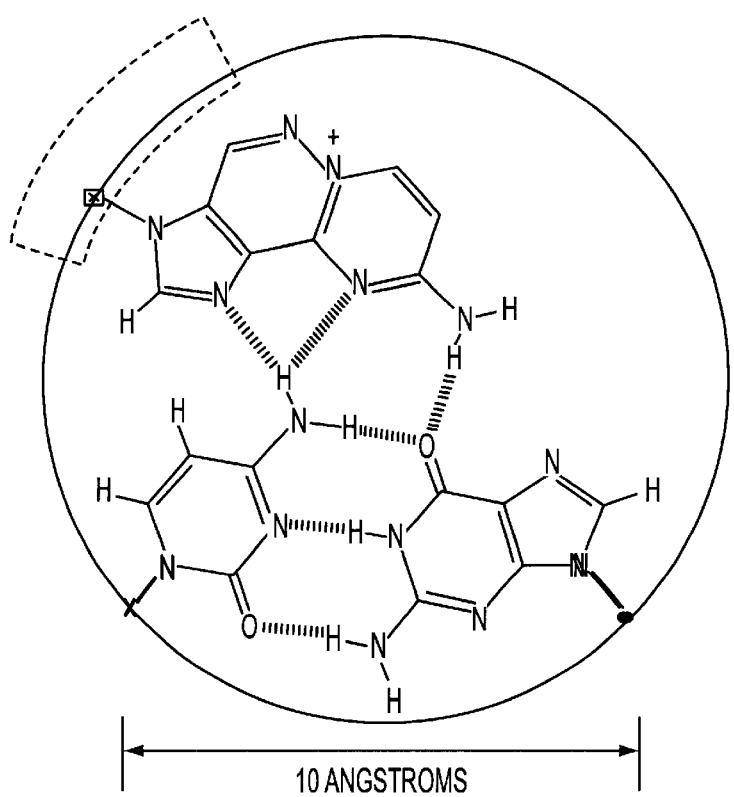

The bases opposite the seven mismatches were chosen because it is known that a G base is the most stable opposite a T-base in the center sequence and a T base the most stable opposite a C base in the center sequence. In addition, this third strand will have little self-structure, which in this case can arise only from hemi-protonation of about one-third of the residues below pH=6, but not at neutrality. This is because the large proportion of T bases do not participate in any self structure. Yet, this sequence does not bind to the target globin sequence with necessary affinity. However, a single composition of matter, which we here denote as N (dentoted as F1 in Example 1 and FIG. 15), may be used to increase very substantially the binding of the third strand to the β globin target sequence, through the residue's designed strong binding to the CG inverted base pair (C in the purine-rich strand). This third strand is presented below, with the remaining three mismatches in boldface.

```
                                            (SEQ ID NO:4)
CCTNGCTCCT/GGGGTTTG/TCTNCCNTTGCTNCCCT
```

This example illustrates the utility of only a single N designed residue targeted to only one of the two inverted base pairs (CG).

EXAMPLES

To illustrate the various aspects and processes of the invention, the following examples of compositions of matter (residues and residue families) designed by the processes of the invention are provided. It is understood that the examples are not intended to limit the invention and that other embodiments of the invention will be apparent from the information provided to those of ordinary skill in the art.

Example 1

Designed Residue to Bind to CG Inverted Base Pairs in Pyrimidine/parallel and the T and G/parallel Motifs Using the computerized Chemical Online Search program, the novel three-ring residue shown in FIG. 14, here called F1, was identified. The F1:CG triplet modelled in two-dimensions is presented in FIGS. 15(a) and 15(b), superimposed on the acceptable-area diagrams for the pyrimidine/parallel (FIG. 9) and T and G/parallel (FIG. 12) motifs, respectively. As can be seen, the F1 glycosyl bond location fits well within the acceptable areas for both motifs. The end of the F1 glycosyl bond, denoted by the square with an x, also fits well within the preferred areas for both motifs, with $r_D$=7.6 Å, $\Theta$=74°, $\zeta$=−10° (see Tables 4, 5 and 6).

In F1, the glycosyl bond is attached to $N_9$, and the base is in the anti-configuration with respect to the sugar. The end of the F1 glycosyl bond is denoted by a square with an x to signify that F1 may be synthesized to have its backbone parallel or antiparallel to the center strand, and here the parallel orientation applies.

In two-dimensional modelling, the F1 residue was positioned by placing the third-strand H-bonds indicated in the figure at the median distances indicated in Table 7 for that type of H-bond. Note that F1 can form one bifurcated H-bond. Literature references to studies of F1 other than for this invention are: Furukawa, Miyashita and Honjio, *Chem. Pharm. Bull.* 22(11): 2552 (1974); Chen, Mieyal and Goldthwait, *Carcinogenesis*, 2(2): 73 (1981). Methods to convert F1 to a phosphoramidite are available and known to those skilled in the art. Hence, it can be incorporated into an appropriate third strand sequence by standard solid phase synthesis methods.

Example 2

Figure 16A:
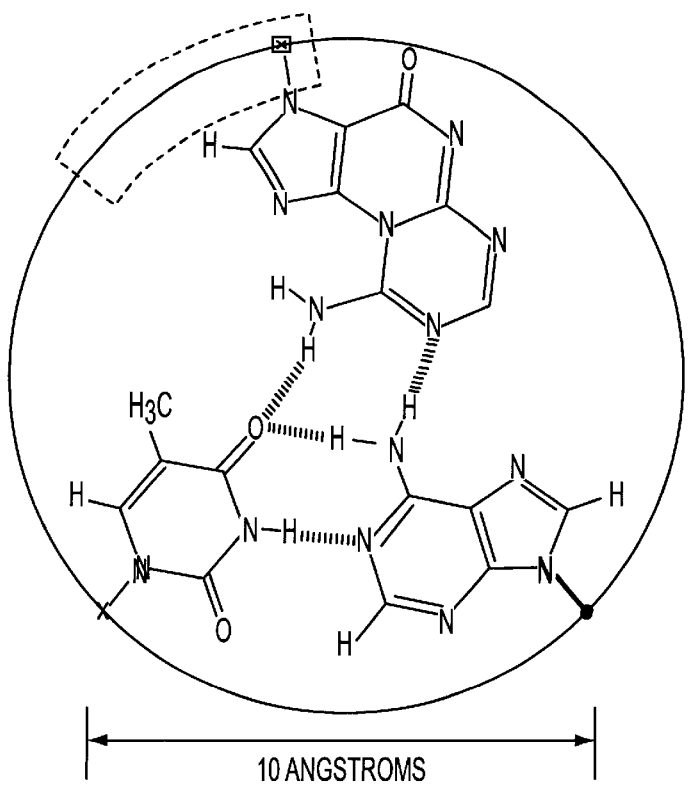
FIG. 16 depicts the designed three-ring heterocycle residue, designated F2, that binds to the inverted TA base pair in the purine/parallel and purine/antiparallel motifs. The F2:TA triplet modelled in two-dimensions and drawn to scale superimposes on the acceptable-area diagrams for the purine/parallel (shown in FIG. 16(a)) and purine/antiparallel (shown in FIG. 16(b)) motifs. With $r_D$=7.9 Å and $\Theta$=121°, the end of the F2 glycosyl bond fits within the acceptable, but not the preferred areas, and the glycosyl bond orientation $\zeta$=0° is within the preferred ranges for both motifs. The glycosyl bond is attached to the $N_7$ position of F2, with F2 in the anti-configuration about the ribose. The end of the F2 glycosyl bond is denoted by a square with an x to signify that F2 may be synthesized to have its backbone either parallel or antiparallel to the center strand (with the thymine base). Here, both the parallel and antiparallel orientations apply. The F2 residue was positioned by placing the third-strand H-bonds at distances indicated in Table 7 for the types of H-bond involved.
Figure 16B:
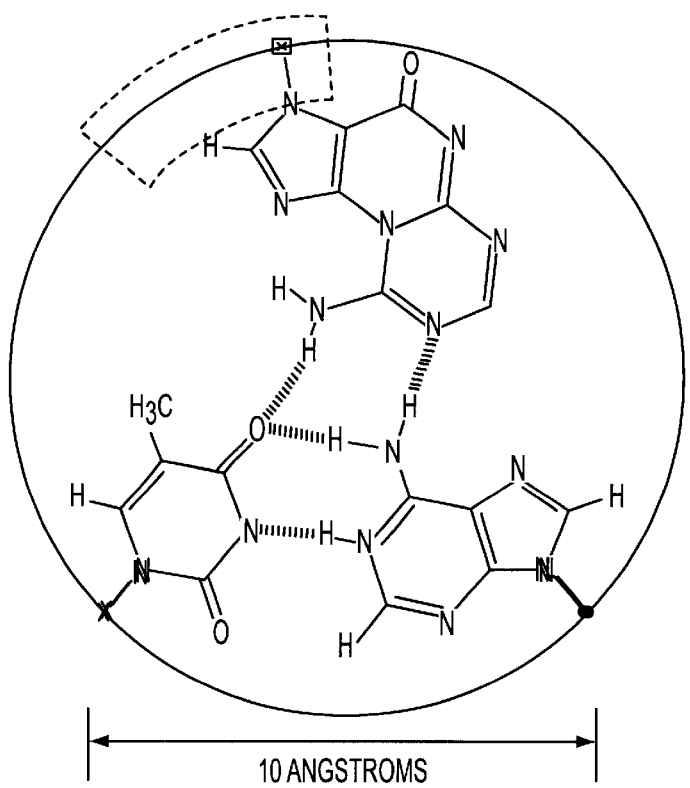

Designed Residue to Bind to TA Inverted Base Pairs in the Purine/parallel and Antiparallel Motifs Using the computerized Chemical Online Search program, the novel three-ring residue in FIG. 14, here called F2, was identified. The F2:TA triplet modelled in two-dimensions is presented in FIG. 16, superimposed on the acceptable-area diagrams for the purine/parallel (FIG. 10) and purine/antiparallel (FIG. 11) motifs. With $r_D$=7.9 Å and $\Theta$=121°, the end of the F2 glycosyl bond, denoted by the square with an x, fits within the acceptable, but not the preferred areas for both motifs. The $\zeta$=0° is in the preferred range for both the purine/parallel and purine/antiparallel motifs. F2 has its glycosyl bond at the $N_7$ ring atom, and the residue is in the anti configuration.

This example illustrates that for TA inverted base pairs the need is for four-ring heterocycles that can H-bond as well as F2, but allow considerably lower $\Theta$ values by utilizing the additional fourth ring for glycosyl bond attachment. Methods to convert F2 to a phosphoramidite are available and known to those skilled in the art. Hence, it can be incorporated into an appropriate third strand sequence by standard solid phase synthesis methods.

Example 3

Figure 17A:
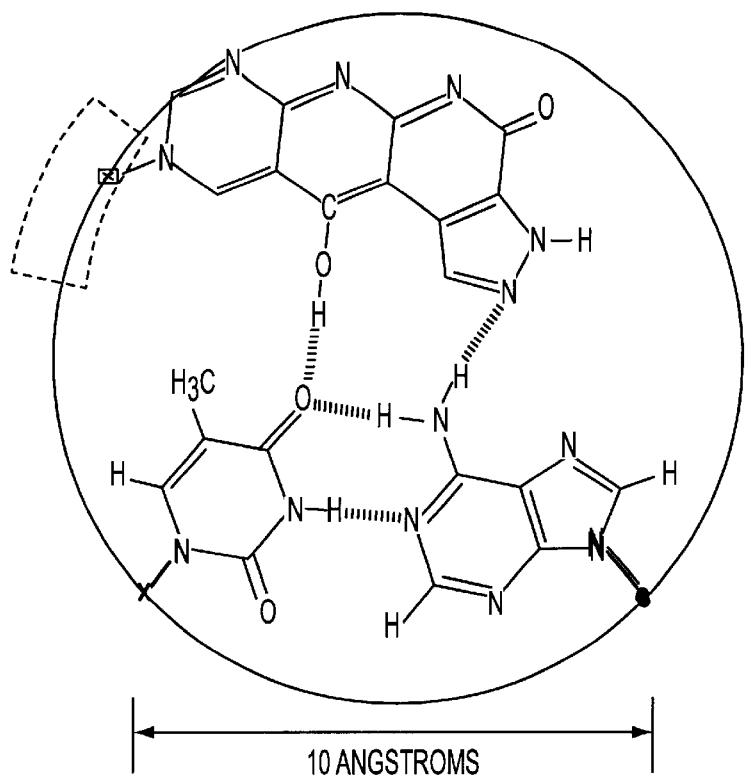
FIG. 17 depicts the designed four-ring heterocycle residue, designated F3, that binds to the inverted TA base pair in the pyrimidine/parallel and T and G/parallel motifs. The F3:TA triplet modelled in two-dimensions and drawn to scale superimposes on the acceptable-area for the pyrimidine/parallel (shown in FIG. 17(a)) and T and G/parallel (shown in FIG. 17(b)) motifs. With $r_D$=6.9 Å and $\Theta$=82°, the end of the F3 glycosyl bond fits within the accepted areas, but not the preferred areas, and the glycosyl bond orientation $\zeta$=−65° is within the acceptable ranges for both motifs. F3 is in the syn-configuration with respect to the ribose. The end of the F3 glycosyl bond is denoted by a square with an x to signify that F3 may be synthesized to have its backbone either parallel or antiparallel to the center strand (with the thymine base). Here, the parallel orientation applies. The F3 residue was positioned by placing the third-strand H-bonds at distances indicated in Table 7 for the types of H-bond.
Figure 17B:
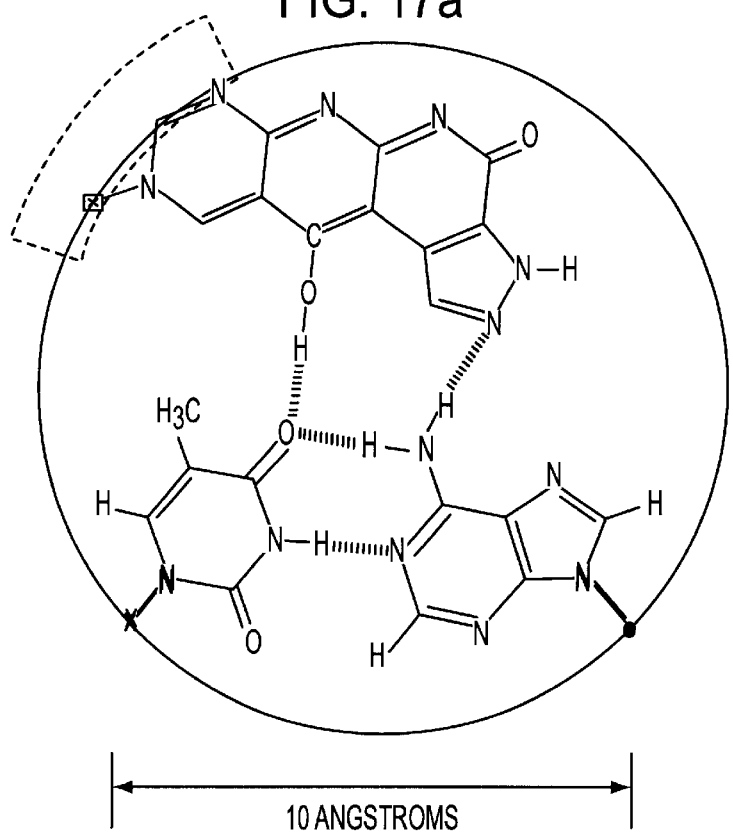

Designed Residue to Bind to TA Inverted Base Pairs in the Pyrimidine/parallel and T and G/parallel Motifs The F3:TA triplet modelled in two-dimensions is superimposed on the acceptable-area diagrams is presented in FIG. 17 for the pyrimidine/parallel (FIG. 9), and T and G/parallel (FIG. 12) motifs. With $r_D=6.9$ Å and $\Theta=82°$, the end of the F3 glycosyl bond, denoted by the square with an x, fits within the acceptable, but not the preferred areas for both motifs. The $\zeta=-65°$ is in the acceptable range for both the pyrimidine/parallel and T and G/parallel motifs. The glycosyl bond is attached to the N atom of the ring at the extreme left. All four rings, with one ring in the extreme left position are necessary to bring the position of the glycosyl bond into conformity with the pyrimidine/parallel motif. In the figure, the end of the F3 glycosyl bond is denoted by a square with an x to signify that F3 may be synthesized to have its backbone parallel or antiparallel to the center strand, and here the parallel orientation applies, with F3 in the syn configuration with respect to the sugar. The F3 residue was positioned by placing the third-strand H-bonds at the median distances indicated in Table 7 for that type of H-bond.

Figure 18:
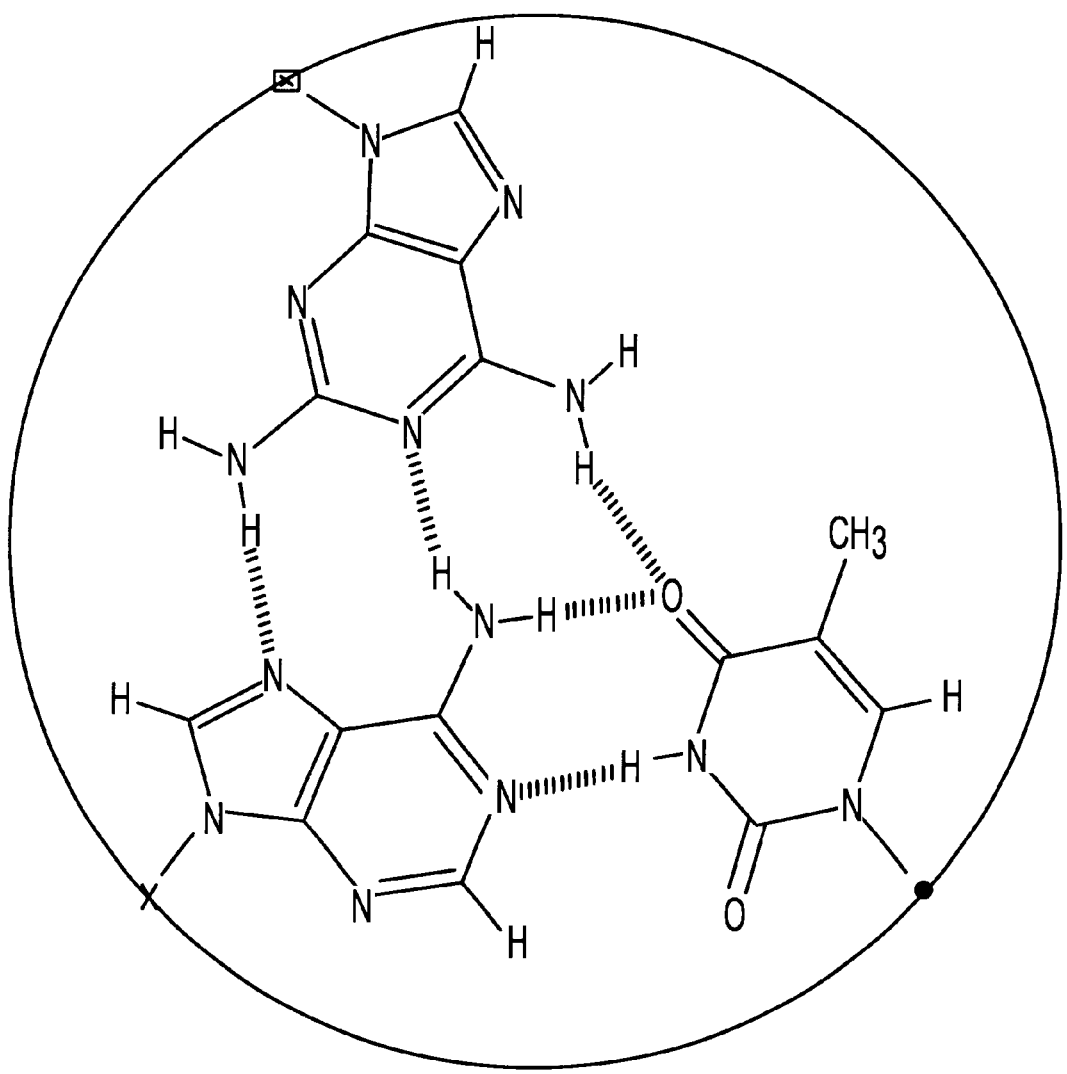
FIG. 18 depicts molecular modelling, drawn to scale, of the 2,6 diaminopurine (D) residue to form a D:AT triplet that is more stable than the A:AT canonical base triplet in the purine/parallel and T and G/parallel motifs. Comparing to FIG. 3, it is apparent that replacement of the hydrogen at $C_2$ of the third-strand adenine with an amino group to make 2,6-diaminopurine allows an additional NH—N strong H-bond with the $N_7$ of the adenine of the direct AT base-pair. The resulting triplet, D:AT has substantially the same geometry as A:AT and will be energetically more favorable than A:AT. With D-circle radius $r_D$=7.6 Å, $\Theta$=104° and $\zeta$=−31°, the designed residue D can serve as a more stable replacement for A in D:AT in the purine/parallel motif where the $r_D$, $\Theta$, and $\zeta$ parameters are all in the preferred range. It can also serve in the purine/antiparallel and T and G/parallel motifs, where $r_D$ and $\Theta$ are in the preferred range and $\zeta$ is in the acceptable range, and perhaps also in the T and G/antiparallel motif, where $r_D$ and $\Theta$ are in the preferred range, and $\zeta$ lies just outside the edge of the acceptable range but within experimental error of the acceptable range.

The F3 residue can be prepared according to Scheme 2, below. Treatment of 1,3-diprotected 5-cyanouracil (VI; MOM=methoxymethyl) with ethyl cyanoacetate will give VII via the ring transformation developed by Su and Watanabe (J. Heterocycl. Chem., 1982, 19, 1962; 1984, 21, 1543–1547; Su, et al., J. Med. Chem, 1986, 29, 709–715). Removal of the MOM protecting groups by HCl in ethanol, followed by chlorination with $PCl_5$ and reduction yields VIII. After saponification of VIII, the free acid will be subjected to Arndt-Estert reaction to extend one carbon unit to give IX in which the methylene group is activated. Treatment of IX with oxalyl chloride X gives the product XI. Sequential treatment of XI with $NaBH_4$, ($CO_2Et$ into $CH_2OH$), $POCl_3$ chlorination, and hydrazine will yield the desired product. Methods to convert F3 to a phosphoramidite are available and known to those skilled in the art. Hence, it can be incorporated into an appropriate third strand sequence by standard solid phase synthesis methods.

over those with canonical base pairs is an object of this invention. Through observation of the A:AT triplet of the purine/parallel motif (FIG. 3), the H-bonding scheme of which was determined by UV resonance Raman spectroscopy, it is apparent that replacing the hydrogen substituent at the $C_2$ position of the third-strand adenine ring with an amino group to make 2,6-diaminopurine, hereafter called D, allows an additional NH---N strong H-bond between $2\text{-}NH_2$ of the third strand D to $N_7$ of the direct AT base-pair. The resulting triplet, D:AT, illustrated in FIG. 18 for the purine/parallel and T and G/parallel motifs, will have substantially the same geometry as A:AT but will be energetically more favorable than A:AT.

With D-circle radius $r_D=7.6$ Å, $\Theta=104°$ and $\zeta=-31°$, the designed residue D can serve as a more stable replacement for A in D:AT in the purine/parallel motif where the $r_D$, $\Theta$, and $\zeta$ parameters are all in the preferred range, and in the purine/antiparallel and T and G/parallel motifs where $r_D$ and $\Theta$ are in the preferred range and $\zeta$ is in the acceptable range, and perhaps in the T and G/parallel motif where $r_D$ and $\Theta$ are in the preferred range, and $\zeta$ lies just outside the edge of the acceptable range but within experimental error of the acceptable range (see Tables 4, 5 and 6).

A phosphoramidite precursor of D, S6-dinitrophenol-2' deoxyguanosine β-cyanoethylphosphoramidite with DMT and dimethylformamidine protecting groups, is commercially available that, after incorporation by solid phase synthesis into a potential third strand of appropriate sequence, can be quantitatively deblocked by standard methods to give the desired third strand containing the D residue (s).

Example 5

Parallel-backbone-orientation Modelling of Inosine (I) that is Known to Bind to Both AT and GC Base Pairs As a test of the ability of the two-dimensional modelling of the invention to predict known third-strand binding, the

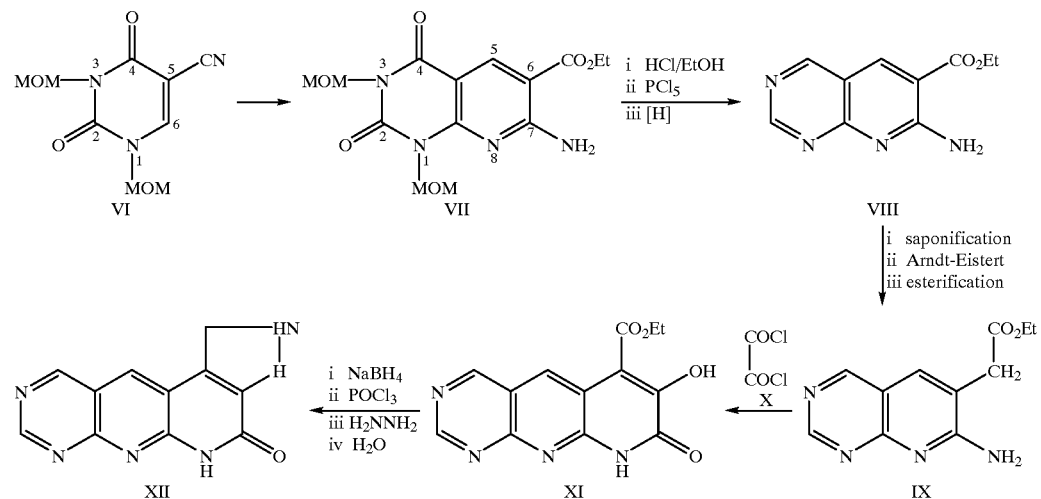

Scheme 2

Example 4

Figure 19:
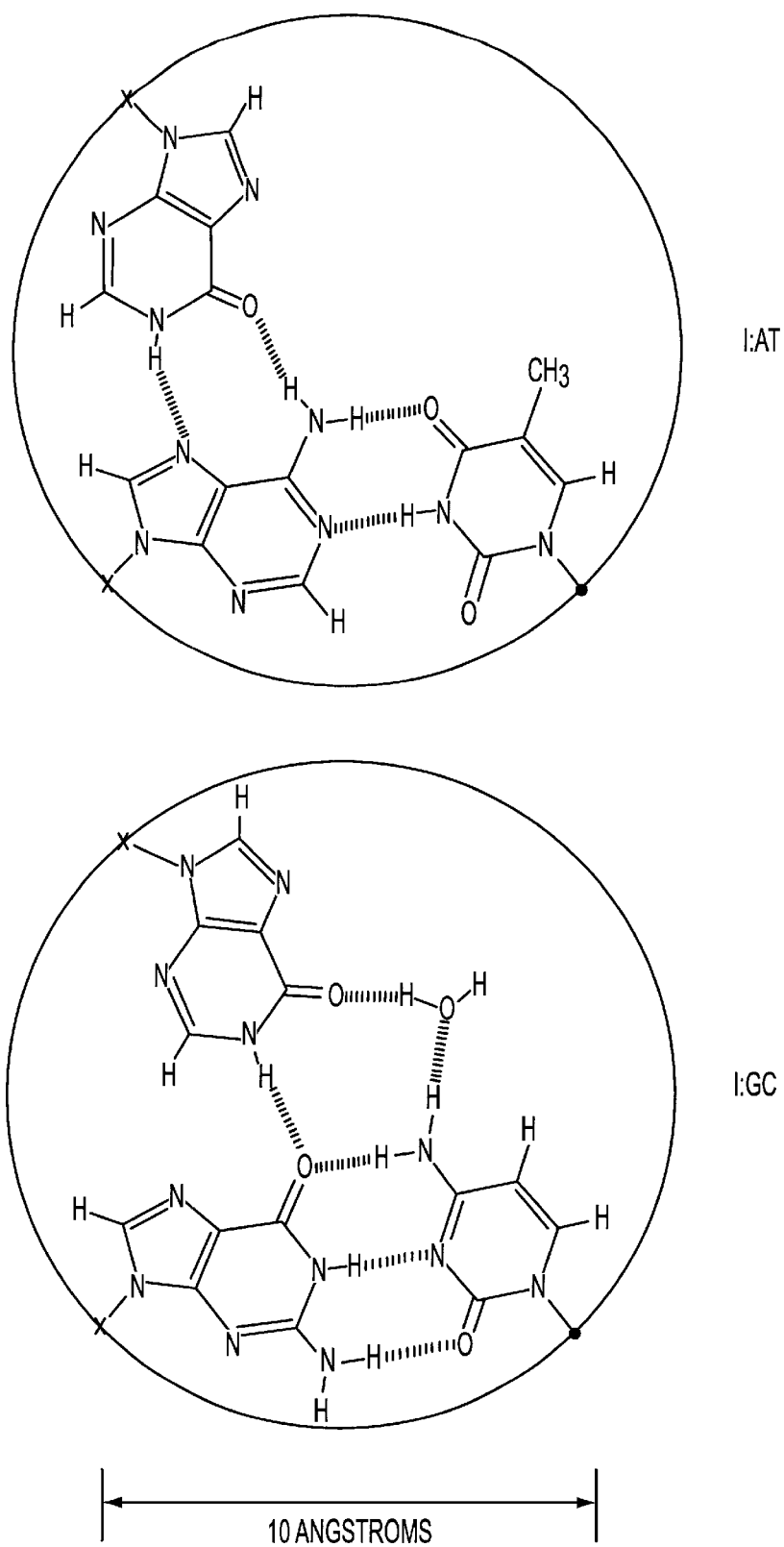
FIG. 19 depicts parallel-backbone-orientation molecular modelling, drawn to scale, of the base hypoxanthine in the nucleoside inosine (I) that is known to bind to both AT and GC direct base pairs. The I:AT and I:GC triplets modelled in two dimensions are shown in (a) and (b), respectively. The third-strand binding code states that the I nucleoside recognizes both AT and GC. $r_D$=7.9 Å, $\Theta$=92° and $\zeta$=0° for I:AT and $r_D$=7.7 Å, $\Theta$=100° and $\zeta$=−26° for I:GC. These small differences in glycosyl-bond parameters between I:AT and I:GC, consistent with the range of differences found in the known motifs, indicate that backbone strain, if any, is acceptable, allowing I third strands to form triplexes containing mixed sequences of I:AT and I:GC triplets.

2,6-diaminopurine as a More Stable Third-strand Residue than A in the Purine/parallel and Other Motifs Identifying novel third-strand residues that bind more stably to direct base pairs to increase the stability of triplexes I:AT and I:GC triplets were modelled (FIG. 19). The third-strand binding code (Table 1) states that the I base recognizes both AT and GC base pairs. In addition, the experiments of Letai, et al. (op. cit.) show that I forms triplexes with homopolymer GC duplexes, homopolymer AT duplexes, and mixed base-pair duplexes with alternating AG in the center strand. Because of the base-sequence symmetry with regard to backbone orientation of homo-duplexes and alternating duplexes, it is not known whether the third strands bind in the parallel, antiparallel, or both orientations.

The modelling indicates that both stable I:AT and I:GC triplets can form in the parallel orientation. Measurements from FIG. 19 find that $r_D$=7.9 Å, $\Theta$=92° and $\zeta$=0° for I:AT and $r_D$=7.8 Å, $\Theta$=93° and $\zeta$=−28° for I:GC. In addition, the small differences in glycosyl-bond parameters between I:AT and I:GC are consistent with the range of differences found in the known motifs (Tables 4, 5 and 6). This indicates that backbone strain, if any, is acceptable, allowing I third strands to form triplexes containing I:AT and I:GC triplets of any sequence. Hence triplexes with mixed AG as well as alternating AG in the center strand will form in accord with experiment.

I:AT and I:GC triplets were also modelled in the antiparallel orientation (illustration not presented). The measurements find that $r_D$=7.3 Å, $\Theta$=138° and $\zeta$=39° for I:AT and $r_D$=7.4 Å, $\Theta$=131° and $\zeta$=52° for I:GC. The similarity of these values between I:AT and I:GC indicate that third-strands of I-homopolymer will form; however, the large $\Theta$ values for both I:AT and I:GC preclude the use of I in place of A and G residues of any third strands to bind in the antiparallel orientation, as the $\Theta$ values fall outside the acceptable ranges for any of those motifs.

Example 6

Designed Residue to Bind to CG Inverted Base Pairs in the Purine/parallel, Purine/antiparallel, T and G/parallel and T and G/antiparallel Motifs This example illustrates that two ring heterocycle residues may be employed as novel residues to fit all motifs except the pyrimidine/parallel motif. The low $\Theta$ values in the pyrimidine/parallel motif require at least three, four-or five-membered ring heterocycles to achieve acceptable $\Theta$ values.

Figure 20:
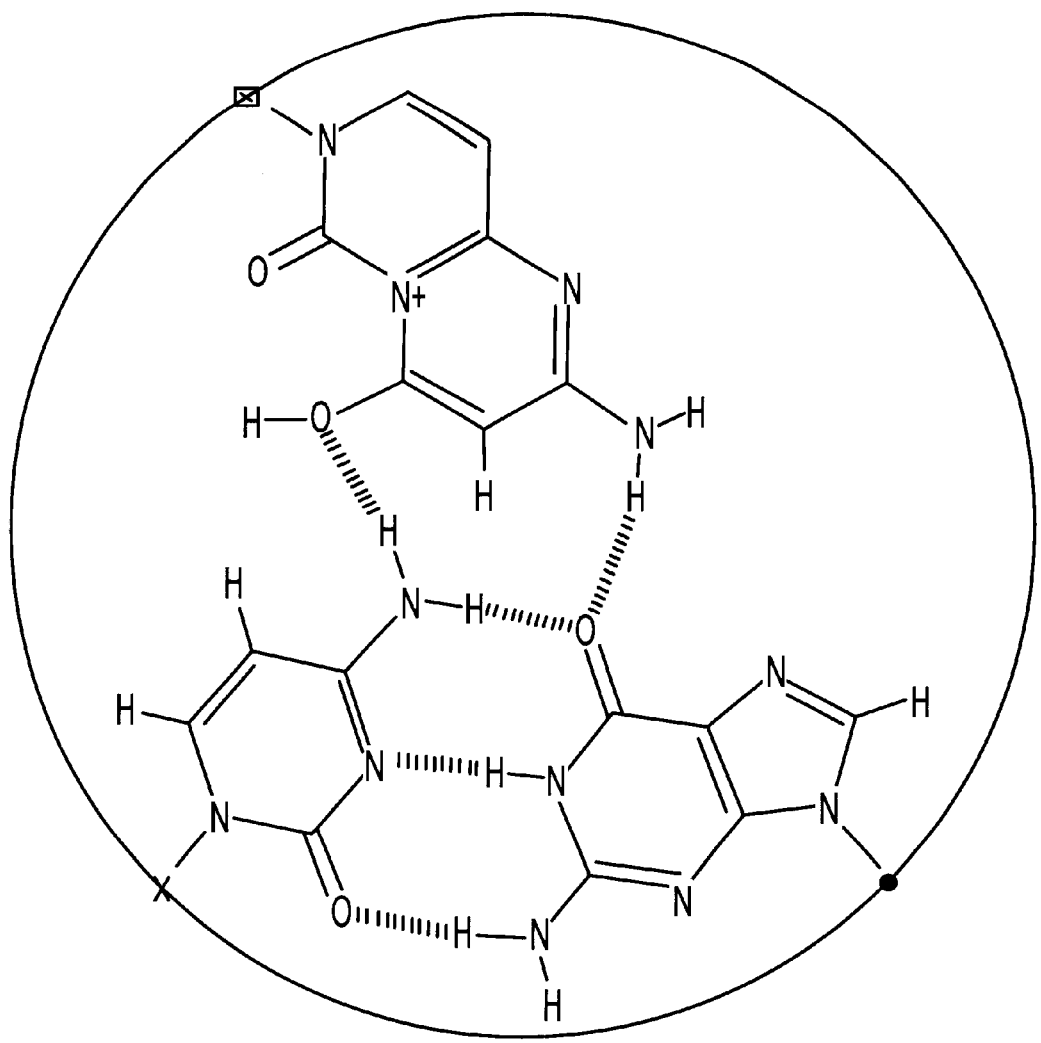
FIG. 20 depicts the designed two-ring heterocycle residue, designated F4, binding to the inverted CG base pair in the purine/parallel, purine/antiparallel, T and G/parallel and T and G/antiparallel motifs, depending on whether the residue is oriented syn or anti about the sugar. The F4:CG triplet is modelled in two-dimensions and drawn to scale. Not shown are the superimpositions on the acceptable-area diagrams for these various motifs. With measurements $r_D$=8.0 Å, $\Theta$=101°, and $\zeta$=−32°, F4 fits in the preferred range of the purine/parallel and T and G/parallel motifs for all three measurements. For the purine/antiparallel and T and G/antiparallel motifs, $r_D$ and $\Theta$ are the same and are in the preferred range, while $\zeta$ is in the acceptable range. The end of the F4 glycosyl bond is denoted by a square with an x to signify that F4 may have its backbone either parallel or antiparallel to the center strand (with the cytosine base). Here, both orientations apply. The F4 residue was positioned by placing the third-strand H-bonds at distances indicated in Table 7 for the types of H-bonds involved.
Figure 20:

The F4:CG triplet is modelled in two dimensions (FIG. 20). With measurements of $r_D$=8.0 Å, $\Theta$=101°, and $\zeta$=−32°, F4 fits in the preferred range of the purine/parallel and T and G/parallel motifs for all three measurements (see Tables 4, 5 and 6). For the purine/antiparallel and T and G/antiparallel motifs, $r_D$ and $\Theta$ are in the preferred range, and $\zeta$ is in the acceptable range. The F4 residue was positioned by placing the third-strand H-bonds at acceptable distances indicated in Table 7 for the types of H-bonds involved.

The F4 residue may be synthesized by the procedure outlined in Scheme 1, below. Treatment of cytosine (I) or cytidine (II) with malonyl chloride (III) in pyridine gives the pyrimido[1,2-a]pyrimidine (IV), which may be treated with ammonia to yield the product (V). As with the other examples of F residues, this two ring system is readily convertable to phosphoramidites for solid phase synthesis of a desired third strand.

Scheme 1

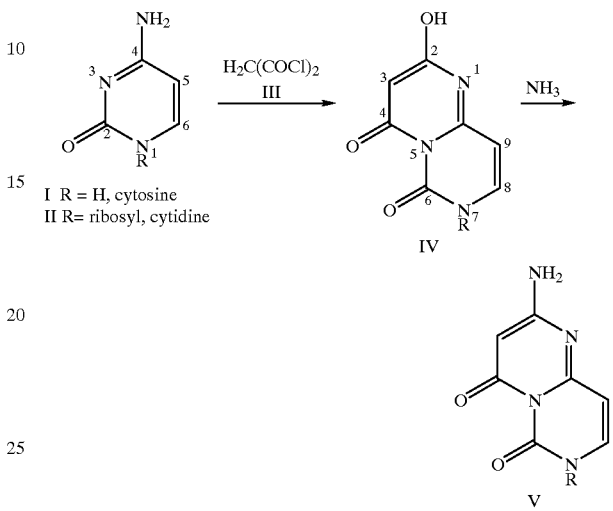

I R = H, cytosine
II R= ribosyl, cytidine

Example 7

Modelling of Residue Disclosed in U.S. Pat. No. 5.405,938

Figure 21:
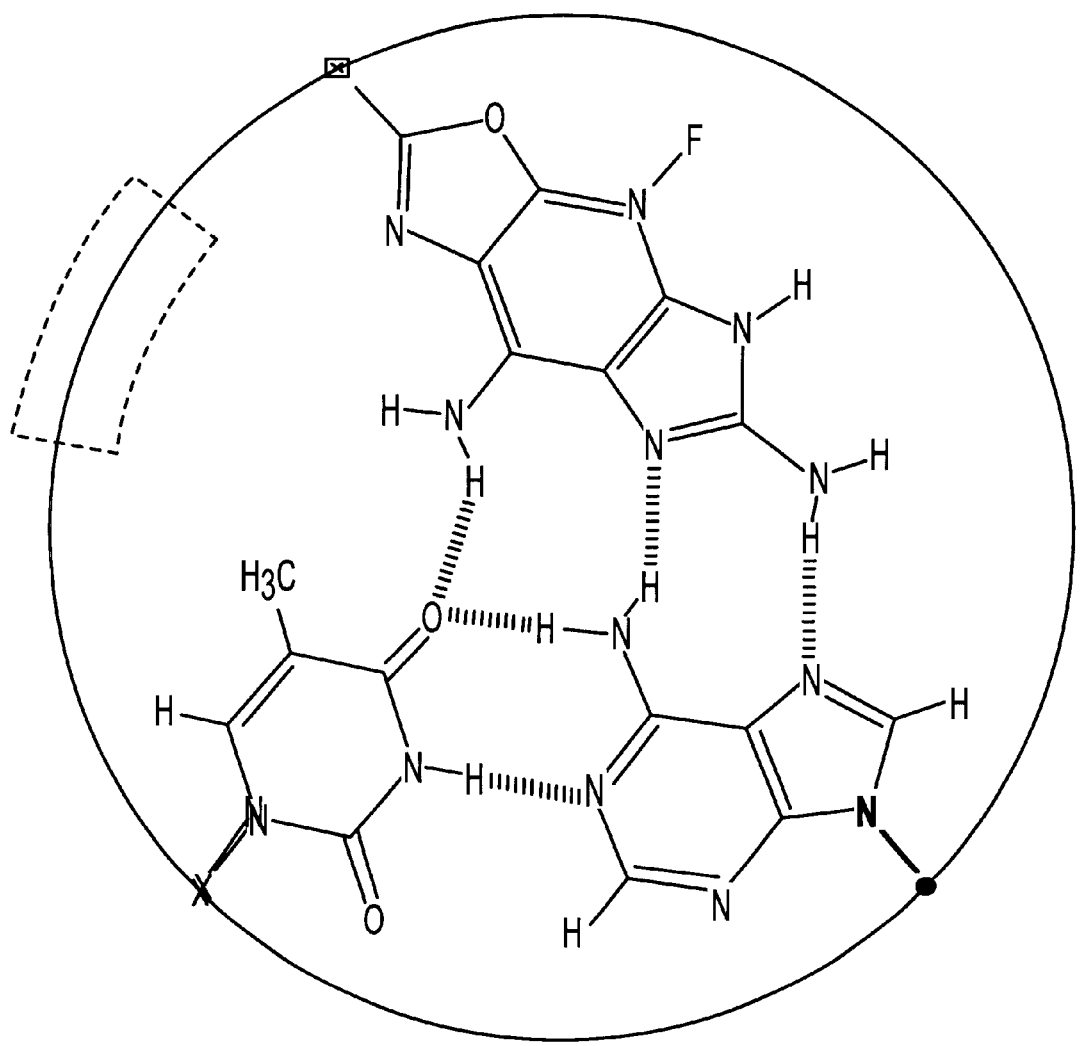
FIG. 21 depicts the designed three ring heterocycle residue of FIG. 14B of U.S. Pat. No. 5,405,938 (designated SW) that, utilizing sugar-phosphate backbones or backbone analogs, will not bind to the inverted TA base pair in the pyrimidine/parallel motif, contrary to what was asserted in that patent. Thus, the SW:TA triplet modelled in two dimensions and drawn to scale does not superimpose on the acceptable area for the pyrimidine/parallel motif. With $r_D$=8.0 Å and $\Theta$=107°, the end of the SW glycosyl bond does not fit within the accepted area due to its large $\Theta$ value. The SW residue was positioned by placing the third strand H-bonds at the distances indicated in Table 7 for the types of H-bond.

Using the rules and guidelines of the present invention, the third strand residue shown in FIG. 14B of U.S. Pat. No. 5,405,938 was modelled as a third strand residue for the pyrimidine/parallel motif. The result is shown in FIG. 21. The SW:TA triplet modelled in two dimensions does not superimpose on the acceptable area for that motif. With $r_D$=8.0 Å and $\zeta$=107°, the end of the SW glycosyl bond does not fit within the accepted area because of its large $\Theta$ value. The SW residue was positioned by placing the third strand H-bonds at distances indicated in Table 7 for the types of H-bond. This residue of U.S. Pat. No. 5,405,938 should not form a stable triplet in the pyrimidine parallel motif with any native sugar-phosphate or analog backbones.

We claim:

1. An oligonucleotide containing a backbone having a polarity associated therewith, and nucleotide bases and at least one synthetic residue bound to the backbone, the bases and residue(s) of said oligonucleotide being effective to bind in a sequence-specific manner to a target sequence of a duplex polynucleotide, said oligonucleotide capable of binding in a parallel orientation relative to a purine-rich or designated core or center strand of said duplex, said nucleotide bases consisting essentially of pyrimidine bases and/or base analogs thereof, and said residue(s) being substantially planar, such that when the oligonucleotide binds to the target sequence, base triplets are formed among each oligonucleotide base or residue and the corresponding bases of the duplex with at least one residue binding to an inverted base pair, and each residue conforms to the following parameters:

a) the radius of the imaginary circle connecting the C1' ends of the two glycosyl bonds of the target base pair of the duplex polynucleotide and the atom of the oligonucleotide backbone which is linked to the corresponding residue of the oligonucleotide is from about 7.0 Å to about 8.6 Å;
   b) the Θ value, measured from the C1' atom bound to the base in the core or center strand, to the atom of the oligonucleotide backbone which is bound to the residue, is from about 53° to about 82°;
   c) the ζ value indicating the angle between said imaginary circle radius passing through the atom of the residue which is bound to the oligonucleotide backbone, and the bond vector between the residue and the oligonucleotide backbone, is from about −90° to about +90°; and
   d) the residue forms a total of at least two hydrogen bonds with one or both bases of the corresponding target base pair of the duplex.

2. An oligonucleotide containing a backbone having a polarity associated therewith, and nucleotide bases and at least one synthetic residue (not 2,6-diaminopurine) bound to the backbone, the bases and residue(s) of said oligonucleotide being effective to bind in a sequence-specific manner to a target sequence of a duplex polynucleotide, said oligonucleotide capable of binding in a parallel orientation relative to a purine-rich or designated core or center strand of said duplex, said nucleotide bases consisting essentially of purine bases and/or base analogs thereof, and said residue(s) being substantially planar, such that when the oligonucleotide binds to the target sequence, base triplets are formed among each oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide backbone which is linked to the corresponding residue of the oligonucleotide is from about 6.7 Å to about 8.6 Å;
   b) the Θ value, measured from the C1' atom bound to the base in the core or center strand, to the atom of the oligonucleotide backbone which is bound to the residue, is from about 81° to about 125°;
   c) the ζ value indicating the angle between said imaginary circle radius passing through the atom of the residue which is bound to the oligonucleotide backbone, and the bond vector between the residue and the oligonucleotide backbone, is from about −100° to about +60°; and d) the residue forms a total of at least two hydrogen bonds with one or both bases of the corresponding target base pair of the duplex.

3. An oligonucleotide containing a backbone having a polarity associated therewith, and nucleotide bases and at least one synthetic residue (not 2,6-diaminopurine) bound to the backbone, the bases and residue(s) of said oligonucleotide being effective to bind in a sequence-specific manner to a target sequence of a duplex polynucleotide, said oligonucleotide capable of binding in an antiparallel orientation relative to a purine-rich or designated core or center strand of said duplex, said nucleotide bases consisting essentially of purine bases and/or base analogs thereof, and said residue(s) being substantially planar, such that when the oligonucleotide binds to the target sequence, base triplets are formed among each oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide backbone which is linked to the corresponding residue of the oligonucleotide is from about 6.5 Å to about 8.6 Å;

b) the Θ value, measured from the C1' atom bound to the base in the core or center strand, to the atom of the oligonucleotide backbone which is bound to the residue, is from about 86° to about 128°;

c) the ζ value indicating the angle between said imaginary circle radius passing through the atom of the residue which is bound to the oligonucleotide backbone, and the bond vector between the residue and the oligonucleotide backbone, is from about −45° to about +120°; and d) the residue forms a total of at least two hydrogen bonds with one or both bases of the corresponding target base pair of the duplex.

4. An oligonucleotide containing a backbone having a polarity associated therewith, and nucleotide bases and at least one synthetic residue (not 2,6-diaminopurine) bound to the backbone, the bases and residue(s) of said oligonucleotide being effective to bind in a sequence-specific manner to a target sequence of a duplex polynucleotide, said oligonucleotide capable of binding in a parallel orientation relative to a purine-rich or designated core or center strand of said duplex, said nucleotide bases consisting essentially of guanine to bind to GC base pairs, and thymine or uracil and/or base analogs thereof, or 2,6-diaminopurine to bind to AT/U base pairs, and said residue(s) being substantially planar, such that when the oligonucleotide binds to the target sequence, base triplets are formed among each oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide backbone which is linked to the corresponding residue of the oligonucleotide is from about 7.0 Å to about 8.6 Å;

b) the Θ value, measured from the C1' atom bound to the base in the core or center strand, to the atom of the oligonucleotide backbone which is bound to the residue, is from about 62° to about 107°;

c) the Θ value indicating the angle between said imaginary circle radius passing through the atom of the residue which is bound to the oligonucleotide backbone, and the bond vector between the residue and the oligonucleotide backbone, is from about −90° to about +90°; and d) the residue forms a total of at least two hydrogen bonds with one or both bases of the corresponding target base pair of the duplex.

5. An oligonucleotide containing a backbone having a polarity associated therewith, and nucleotide bases and at least one synthetic residue (not 2,6-diaminopurine) bound to the backbone, the bases and residue(s) of said oligonucleotide being effective to bind in a sequence-specific manner to a target sequence of a duplex polynucleotide, said oligonucleotide capable of binding in an antiparallel orientation relative to a purine-rich or designated core or center strand of said duplex, said nucleotide bases consisting essentially of guanine to bind to GC base pairs, and thymine or uracil and/or base analogs thereof or 2,6-diaminopurine to bind to AT/U base pairs, and said residue(s) being substantially planar, such that when the oligonucleotide binds to the target sequence, base triplets are formed among each oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide backbone which is linked to the corresponding residue of the oligonucleotide is from about 5.9 Å to about 8.2 Å;

b) the Θ value, measured from the C1' atom bound to the base in the core or center strand, to the atom of the oligonucleotide backbone which is bound to the residue, is from about 90° to about 110°;

c) the ζ value indicating the angle between said imaginary circle radius passing through the atom of the residue which is bound to the oligonucleotide backbone, and the bond vector between the residue and the oligonucleotide backbone, is from about −30° to about +120°; and d) the residue forms a total of at least two hydrogen bonds with one or both bases of the corresponding target base pair of the duplex.

6. An oligonucleotide analog containing a backbone having no polarity associated therewith, and nucleotide bases and at least one synthetic residue bound to the backbone, the bases and residue(s) of said oligonucleotide analog being effective to bind in a sequence-specific manner to a target sequence of a duplex polynucleotide, said oligonucleotide analog capable of binding to a purine-rich or designated core or center strand of said duplex, said nucleotide bases consisting essentially of pyrimidine bases and/or base analogs thereof, and said residue(s) being substantially planar, such that when the oligonucleotide analog binds to the target sequence, base triplets are formed among each analog oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide analog backbone which is linked to the corresponding residue of the oligonucleotide analog is from about 7.0 Å to about 8.6 Å;

b) the Θ value, measured from the C1' atom bound to the base in the core or center strand, to the atom of the oligonucleotide analog backbone which is bound to the residue, is from about 53° to about 82°;

c) the ζ value indicating the angle between said imaginary circle radius passing through the atom of the residue which is bound to the oligonucleotide analog backbone, and the bond vector between the residue and the oligonucleotide analog backbone, is from about −90° to about +90°; and d) the residue forms a total of at least two hydrogen bonds with one or both bases of the corresponding target base pair of the duplex.

7. An oligonucleotide analog containing a backbone having no polarity associated therewith, and nucleotide bases and at least one synthetic residue bound to the backbone, the bases and residue(s) of said oligonucleotide analog being effective to bind in a sequence-specific manner to a target sequence of a duplex polynucleotide, said oligonucleotide analog capable of binding to a purine-rich or designated core or center strand of said duplex, said nucleotide bases consisting essentially of purine bases and/or base analogs thereof, or 2,6-diaminopurine, and said residue(s) being substantially planar, such that when the oligonucleotide analog binds to the target sequence, base triplets are formed among each analog oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide analog backbone which is linked to the corresponding residue of the oligonucleotide analog is from about 6.7 Å to about 8.6 Å;

b) the Θ value, measured from the C1' atom bound to the base in the core or center strand, to the atom of the oligonucleotide analog backbone which is bound to the residue, is from about 81° to about 125°;

c) the ζ value indicating the angle between said imaginary circle radius passing through the atom of the residue which is bound to the oligonucleotide analog backbone, and the bond vector between the residue and the oligonucleotide analog backbone, is from about −100° to about +60°; and d) the residue forms a total of at least two hydrogen bonds with one or both bases of the corresponding target base pair of the duplex.

8. An oligonucleotide analog containing a backbone having no polarity associated therewith, and nucleotide bases and at least one synthetic residue bound to the backbone, the bases and residue(s) of said oligonucleotide analog being effective to bind in a sequence-specific manner to a target sequence of a duplex polynucleotide, said oligonucleotide analog capable of binding to a purine-rich or designated core or center strand of said duplex, said nucleotide bases consisting essentially of purine bases and/or base analogs thereof, or 2,6-diaminopurine, and said residue(s) being substantially planar, such that when the oligonucleotide analog binds to the target sequence, base triplets are formed among each analog oligonucleotide base or residue and the corresponding bases of the target base pair of the duplex, and each residue conforms to the following parameters:

a) the radius of the imaginary circle connecting the C1' ends of the two glycosyl bonds of the target base pair of the duplex polynucleotide and the atom of the oligonucleotide analog backbone which is linked to the corresponding residue of the oligonucleotide analog is from about 6.5 Å to about 8.6 Å;

b) the Θ value, measured from the C1' atom bound to the base in the core or center strand, to the atom of the oligonucleotide analog backbone which is bound to the residue, is from about 86° to about 128°;

c) the ζ value indicating the angle between said imaginary circle radius passing through the atom of the residue which is bound to the oligonucleotide analog backbone, and the bond vector between the residue and the oligonucleotide analog backbone, is from about −45° to about +120°; and d) the residue forms a total of at least two hydrogen bonds with one or both bases of the corresponding target base pair of the duplex.

9. An oligonucleotide analog containing a backbone having no polarity associated therewith, and nucleotide bases and at least one synthetic residue bound to the backbone, the bases and residue(s) of said oligonucleotide analog being effective to bind in a sequence-specific manner to a target sequence of a duplex polynucleotide, said oligonucleotide analog capable of binding to a purine-rich or designated core or center strand of said duplex, said nucleotide bases consisting essentially of guanine to bind to GC base pairs, and thymine or uracil or base analogs thereof or 2,6-diaminopurine to bind to AT/U base pairs, and said residue (s) being substantially planar, such that when the oligonucleotide analog binds to the target sequence, base triplets are formed among each analog oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide analog backbone which is linked to the corresponding residue of the oligonucleotide analog is from about 7.0 Å to about 8.6 Å;

b) the Θ value, measured from the C1' atom bound to the base in the core or center strand, to the atom of the oligonucleotide analog backbone which is bound to the residue, is from about 62° to about 107°;

c) the ζ value indicating the angle between said imaginary circle radius passing through the atom of the residue which is bound to the oligonucleotide analog backbone, and the bond vector between the residue and the oligonucleotide analog backbone, is from about −90° to about +90°; and d) the residue forms a total of at least two hydrogen bonds with one or both bases of the corresponding target base pair of the duplex.

10. An oligonucleotide analog containing a backbone having no polarity associated therewith, and nucleotide bases and at least one synthetic residue bound to the backbone, the bases and residue(s) of said oligonucleotide analog being effective to bind in a sequence-specific manner to a target sequence of a duplex polynucleotide, said oligonucleotide analog capable of binding to a purine-rich or designated core or center strand of said duplex, said nucleotide bases consisting essentially of guanine to bind to GC base pairs, and thymine or uracil and/or base analogs thereof or 2,6-diaminopurine to bind to AT/U base pairs, and said residue(s) being substantially planar, such that when the oligonucleotide analog binds to the target sequence, base triplets are formed among each analog oligonucleotide base or residue and the corresponding bases of the duplex, and each residue conforms to the following parameters:

a) the radius of the imaginary circle connecting the C1' ends of the two glycosyl bonds of the target base pair of the duplex polynucleotide and the atom of the oligonucleotide analog backbone which is linked to the corresponding residue of the oligonucleotide analog is from about 5.9 Å to about 8.2 Å;

b) the $\Theta$ value, measured from the C1' atom bound to the base in the core or center strand, to the atom of the oligonucleotide analog backbone which is bound to the residue, is from about 90° to about 110°;

c) the $\zeta$ value indicating the angle between said imaginary circle radius passing through the atom of the residue which is bound to the oligonucleotide analog backbone, and the bond vector between the residue and the oligonucleotide analog backbone, is from about −30° to about +120°; and d) the residue forms a total of at least two hydrogen bonds with one or both bases of the corresponding target base pair of the duplex.

11. The oligonucleotide of any one of claims 1–5, wherein the backbone is a native sugar-phosphate backbone.

12. The oligonucleotide of any one of claims 1–5, wherein the backbone is an analog backbone.

13. The oligonucleotide of claim 12, wherein the backbone is selected from the group consisting of phosphorothioate, methylphosphonate, peptide and mixtures thereof.

14. The oligonucleotide of any one of claims 1–10, wherein the residue is selected from the group consisting of F1, F2, F3 and F4 as shown in FIG. 14.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 36 base pairs
      (B) TYPE: nucleic acid
      (C) STRANDEDNESS: double
      (D) TOPOLOGY: linear (xi) SEQUENCE DESCRIPTION: SEQ ID NO:1:

```
                              -continued

CCTGACTCCT GAGGAGAAGT CTGCCGTTAC TGCCCT                              36

(2) INFORMATION FOR SEQ ID NO:2:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (xi) SEQUENCE DESCRIPTION: SEQ ID NO:2:

CCTGACTCCT GTGGAGAAGT CTGCCGTTAC TGCCCT                              36

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:3:

TCCCTTCGTT TCCTTCTGTT GTGGGGTCCT CGTTCC                              36

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:4:

TCCCNTCGTT NCCNTCTGTT GTGGGGTCCT CGNTCC                              36
```